United States Patent
Bunner et al.

(10) Patent No.: US 9,764,323 B2
(45) Date of Patent: Sep. 19, 2017

(54) DEVICE AND METHODS USING POROUS MEDIA IN FLUIDIC DEVICES

(71) Applicant: Waters Technologies Corporation, Milford, MA (US)

(72) Inventors: Bernard Bunner, Newton, MA (US); Martin Gilar, Franklin, MA (US); Robert A. Jencks, Mendon, MA (US); Charles T. Murphy, Norton, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 84 days.

(21) Appl. No.: 14/489,855

(22) Filed: Sep. 18, 2014

(65) Prior Publication Data
US 2016/0082435 A1    Mar. 24, 2016

(51) Int. Cl.
*B01L 3/00* (2006.01)
*G01N 30/60* (2006.01)

(52) U.S. Cl.
CPC ... *B01L 3/502753* (2013.01); *B01L 3/502746* (2013.01); *G01N 30/603* (2013.01); *G01N 30/6095* (2013.01); *B01L 3/502707* (2013.01); *B01L 3/502715* (2013.01); *B01L 2200/027* (2013.01); *B01L 2300/0681* (2013.01); *B01L 2400/0487* (2013.01); *B01L 2400/086* (2013.01)

(58) Field of Classification Search
USPC .......................................................... 422/503
See application file for complete search history.

(56) References Cited

U.S. PATENT DOCUMENTS

| 5,370,692 A | 12/1994 | Fink et al. |
| 6,139,757 A * | 10/2000 | Ohmura ................. B01D 61/18 210/351 |
| 6,168,948 B1 | 1/2001 | Anderson et al. |
| 6,211,424 B1 | 4/2001 | Powell et al. |
| 6,527,951 B1 | 3/2003 | Tuvim |

(Continued)

FOREIGN PATENT DOCUMENTS

| EP | 2597460 A1 | 5/2013 |
| JP | 2007256226 A | 10/2007 |

(Continued)

OTHER PUBLICATIONS

"Combined Search and Examination Report Under Sections 17 & 18(3)", Application No. GB1516296.9, Feb. 29, 2016, 10 pages.

*Primary Examiner* — Jill Warden
*Assistant Examiner* — Brittany Fisher
(74) *Attorney, Agent, or Firm* — Guntin & Gust, PLC; Ralph Trementozzi

(57) ABSTRACT

A system that incorporates teachings of the subject disclosure may include, for example, a process that includes obtaining a porous medium comprising a porous material having a first shape and an initial porosity profile. The porous medium is engaged with a cavity in a fluidic device, wherein the cavity is in fluid communication with a channel of the fluidic device. The first shape of the porous material can be adjusted to a second shape resulting in the initial porosity profile being adjusted to a target porosity profile. Such adjustment can be accomplished by the engaging of the porous medium with the cavity, by pre-adjusting a shape of the porous media before insertion into the cavity, or by some combination thereof. Other embodiments are disclosed.

19 Claims, 19 Drawing Sheets

(56) References Cited

U.S. PATENT DOCUMENTS

| | | |
|---|---|---|
| 7,204,264 B2 | 4/2007 | Crocker et al. |
| 7,841,190 B2 | 11/2010 | Gerhardt et al. |
| 7,887,754 B2 | 2/2011 | Granger et al. |
| 7,938,961 B2 | 5/2011 | Plumb et al. |
| 8,409,443 B2 | 4/2013 | Gilar et al. |
| 8,449,769 B2 * | 5/2013 | Belanger ................ G01N 30/08 210/198.2 |
| 8,580,560 B1 | 11/2013 | Ellis et al. |
| 8,671,975 B2 | 3/2014 | Charlton et al. |
| 8,685,239 B2 | 4/2014 | Granger et al. |
| 2003/0150806 A1 | 8/2003 | Hobbs et al. |
| 2004/0018116 A1 * | 1/2004 | Desmond ............... B01L 3/5027 422/502 |
| 2004/0142488 A1 | 7/2004 | Gierde et al. |
| 2005/0006293 A1 | 1/2005 | Koehler et al. |
| 2005/0072670 A1 * | 4/2005 | Hasegawa ............. C12Q 1/001 204/403.01 |
| 2006/0060515 A1 | 3/2006 | Benevides et al. |
| 2006/0219636 A1 | 10/2006 | Plumb et al. |
| 2007/0031283 A1 * | 2/2007 | Davis ................... A61B 5/1411 422/400 |
| 2007/0116600 A1 * | 5/2007 | Kochar ................. G01N 21/76 422/65 |
| 2007/0141325 A1 | 6/2007 | O'Gara et al. |
| 2007/0295663 A1 * | 12/2007 | Iraneta ................ G01N 30/603 210/656 |
| 2008/0230951 A1 | 9/2008 | Dannoux et al. |
| 2008/0257835 A1 | 10/2008 | Benevides et al. |
| 2008/0302423 A1 | 12/2008 | Gerhardt et al. |
| 2009/0269859 A1 | 10/2009 | Liu |
| 2010/0018928 A1 | 1/2010 | Charlton et al. |
| 2011/0100100 A1 | 5/2011 | Strand et al. |
| 2011/0107822 A1 | 5/2011 | Bunner et al. |
| 2011/0272356 A1 | 11/2011 | Hoffmann |
| 2011/0278214 A1 | 11/2011 | Benevides et al. |
| 2012/0040448 A1 | 2/2012 | Gremetz et al. |
| 2012/0132794 A1 | 5/2012 | Buchanan et al. |
| 2012/0269694 A1 * | 10/2012 | Zheng ................... C01B 3/065 422/187 |
| 2013/0014567 A1 | 1/2013 | Bunner et al. |
| 2013/0053588 A1 | 2/2013 | Iraneta et al. |
| 2013/0133760 A1 | 5/2013 | Bunner et al. |
| 2013/0134083 A1 | 5/2013 | Benevides et al. |
| 2013/0256231 A1 | 10/2013 | Belanger et al. |
| 2014/0021116 A1 | 1/2014 | Ford et al. |
| 2014/0053910 A1 | 2/2014 | Bunner et al. |
| 2014/0138312 A1 | 5/2014 | Bunner |

FOREIGN PATENT DOCUMENTS

| | | |
|---|---|---|
| WO | 2008121453 A2 | 10/2008 |
| WO | 2010/102194 | 9/2010 |
| WO | 2014197783 A1 | 12/2014 |
| WO | 2015179430 | 11/2015 |

* cited by examiner

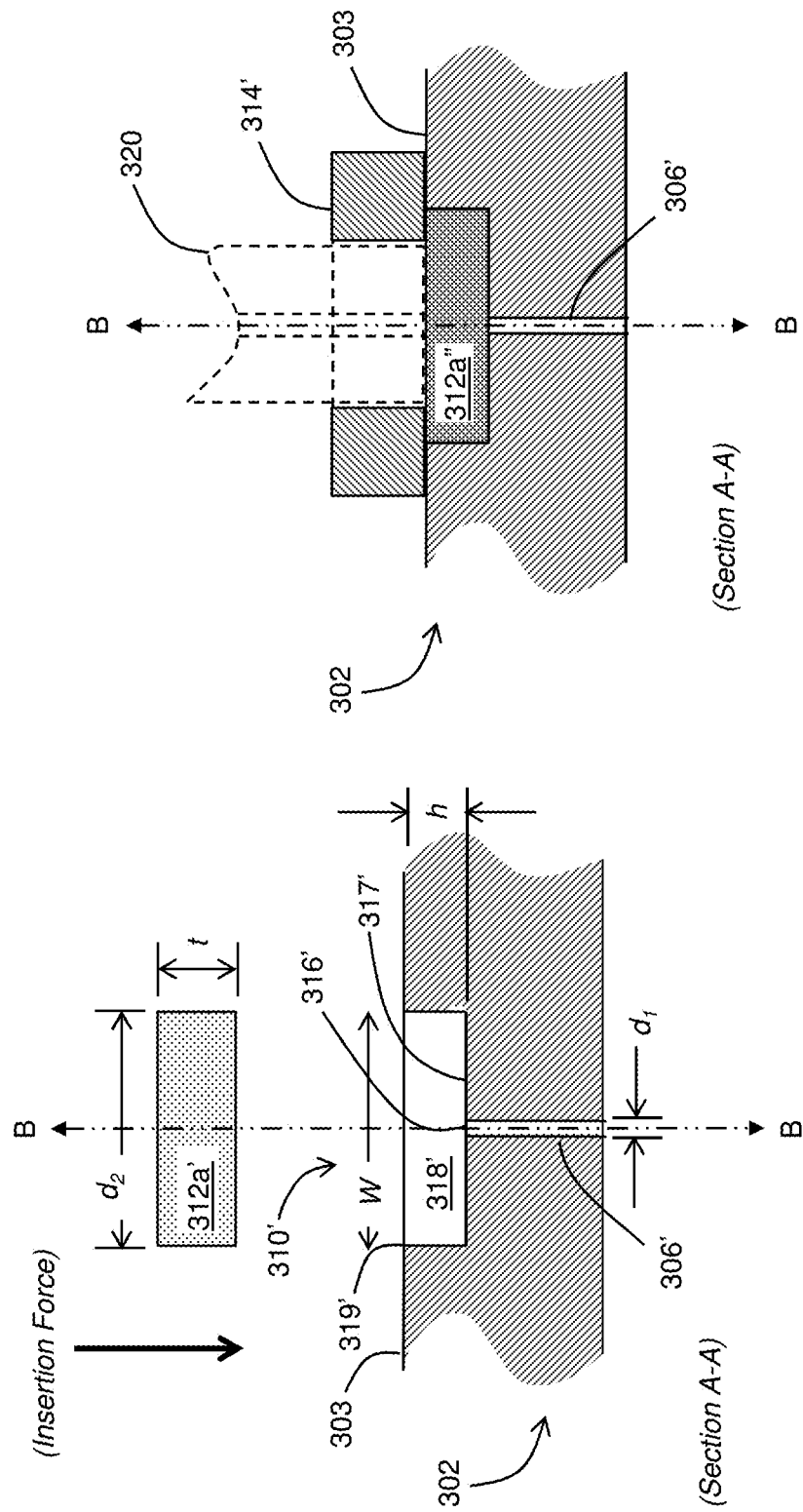

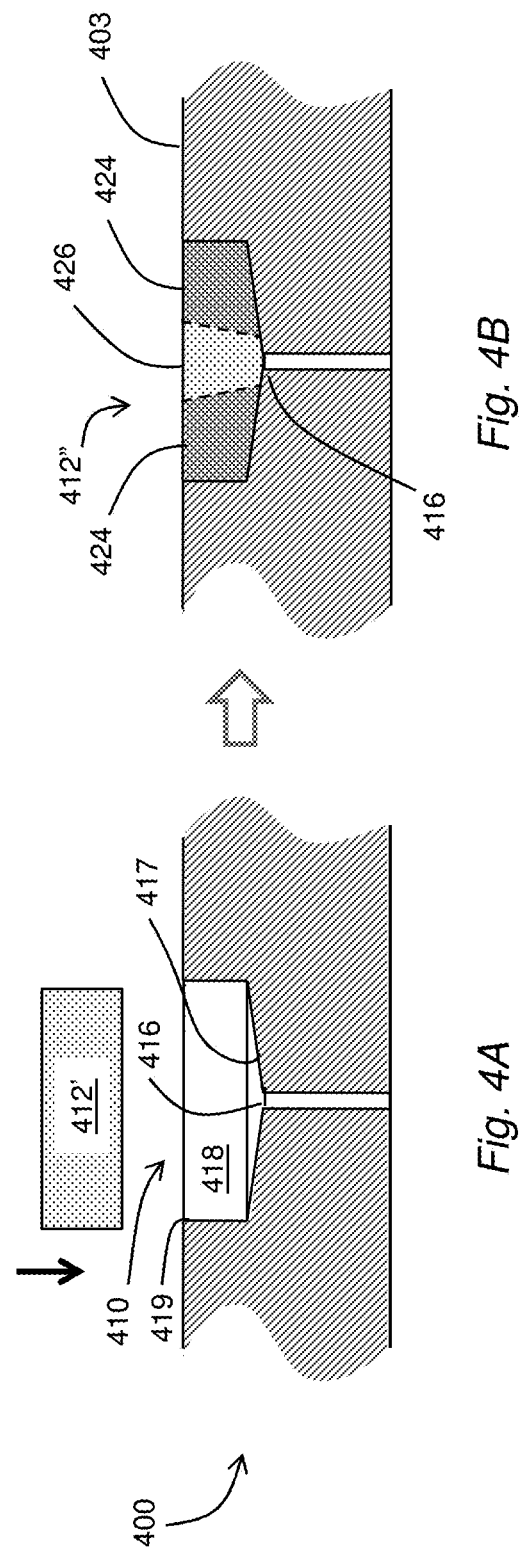

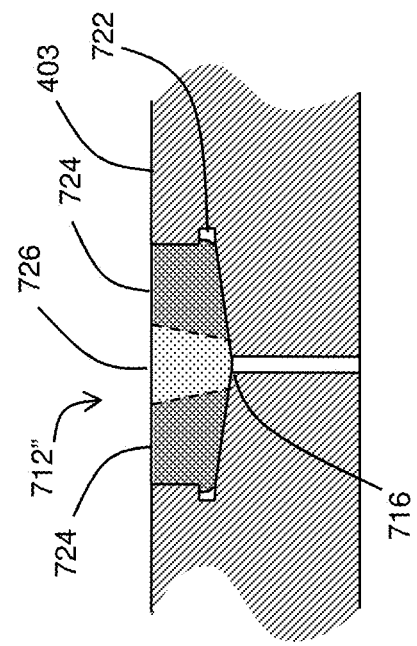
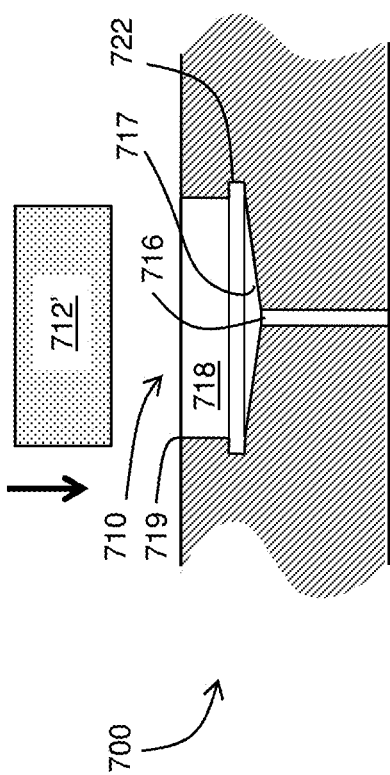
Fig. 7B
Fig. 7A

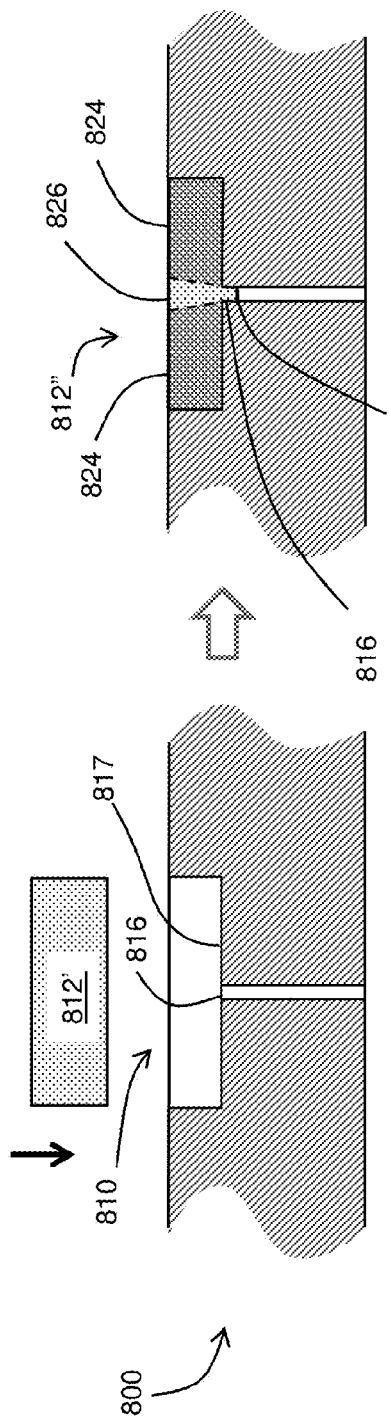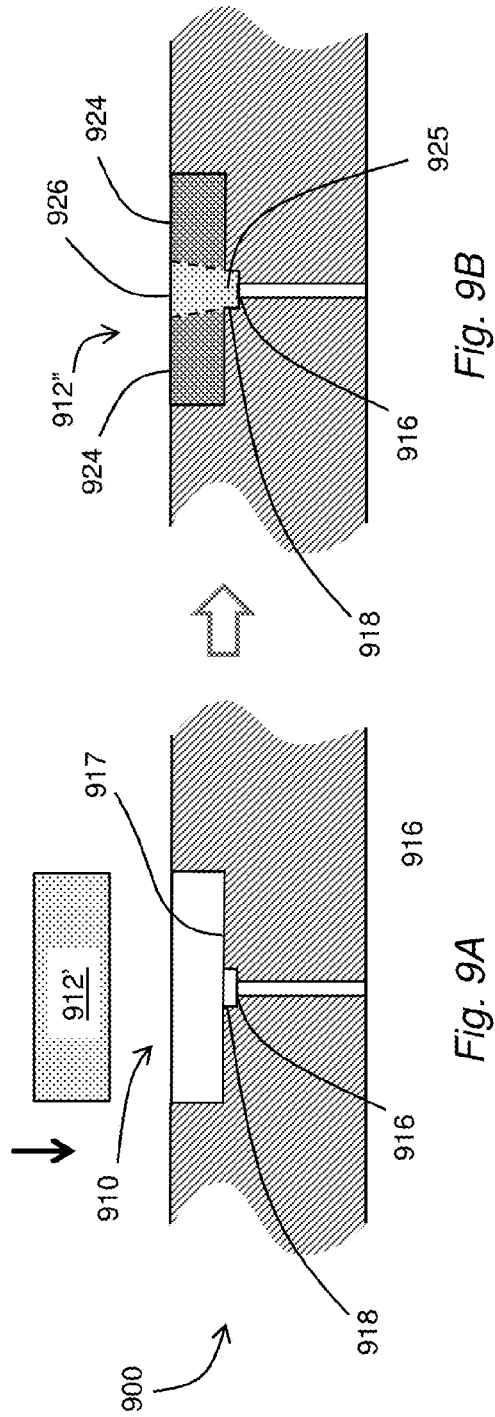

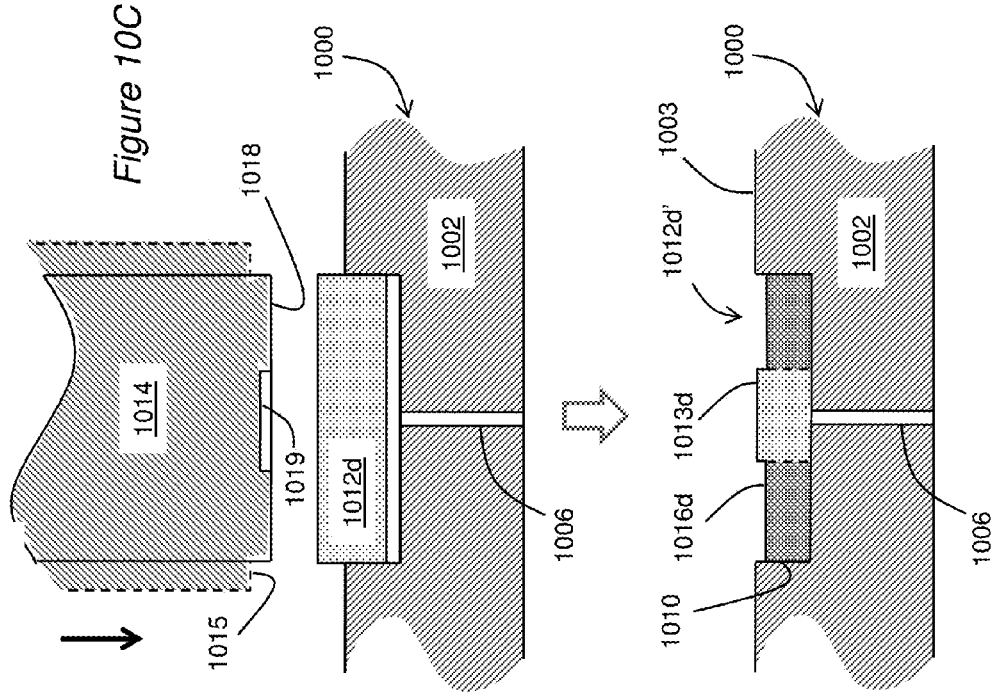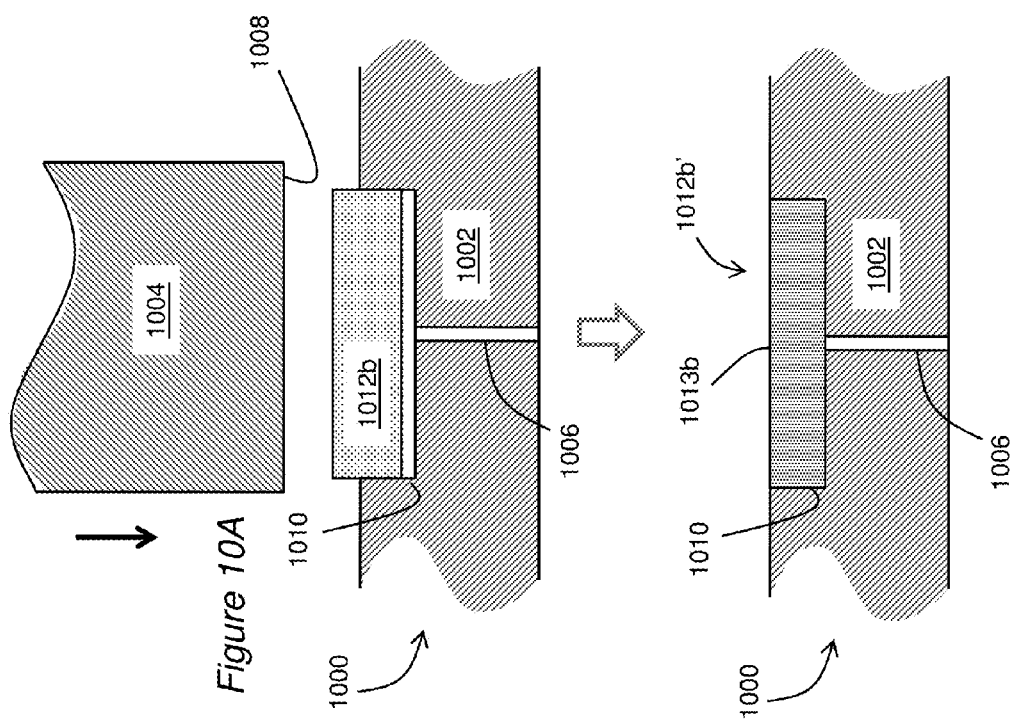

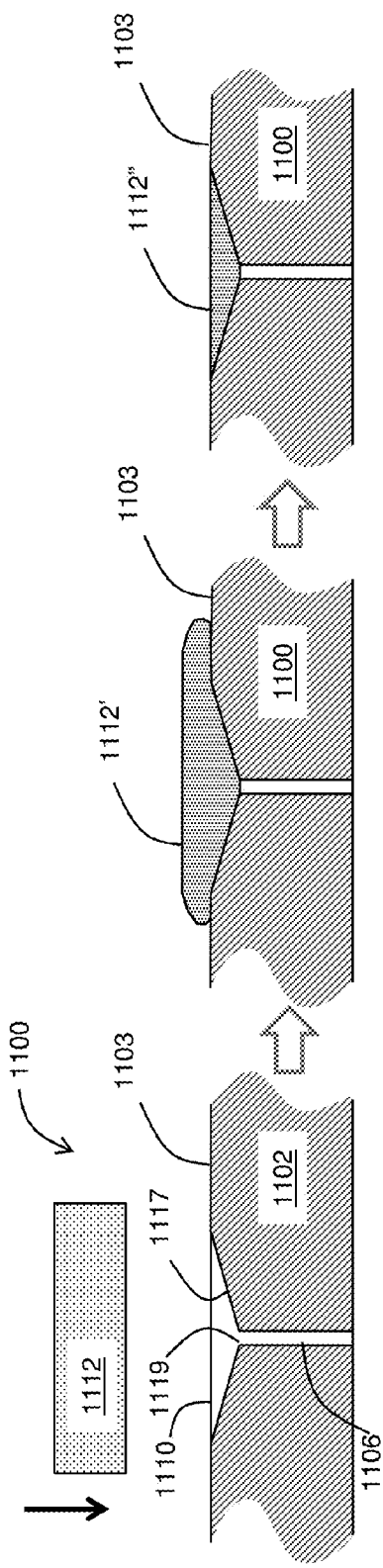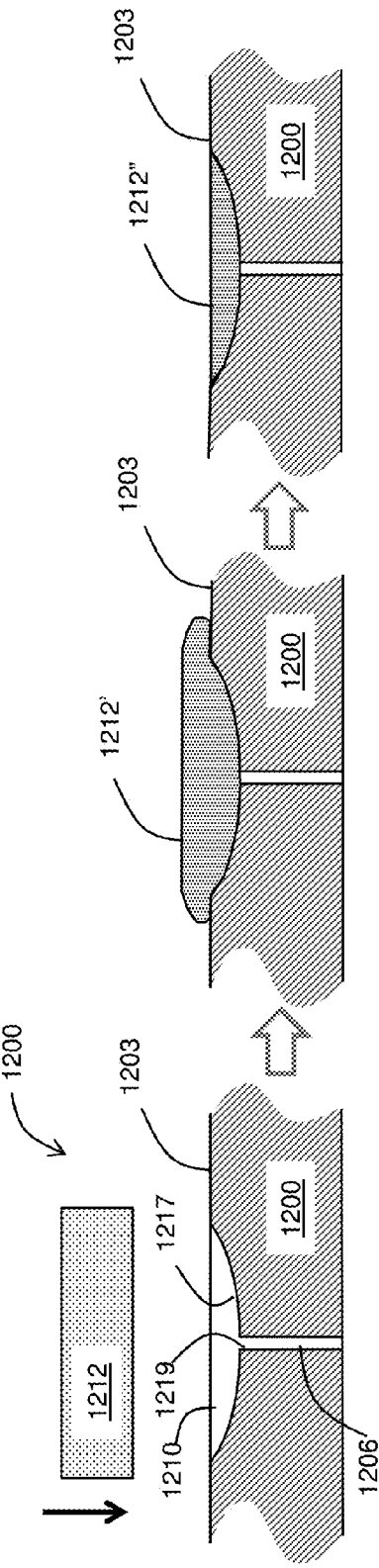

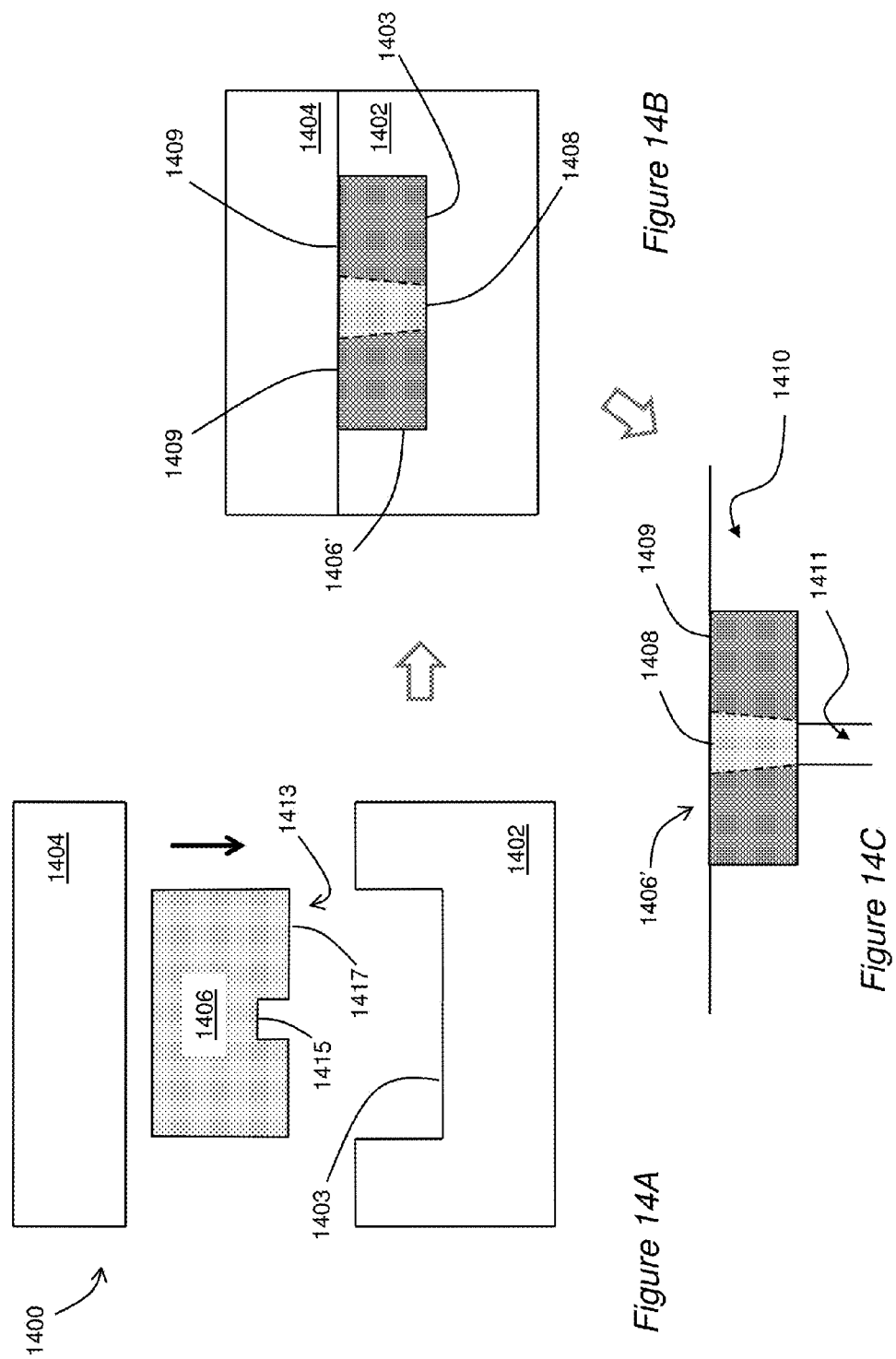

DEVICE AND METHODS USING POROUS MEDIA IN FLUIDIC DEVICES

FIELD OF THE DISCLOSURE

The subject disclosure relates to a device and methods using porous media in fluidic devices.

BACKGROUND

Microfluidic liquid chromatography (LC) columns, or chips, packed with chromatographic particles require frits at an outlet and in most cases at an inlet of the column in order to retain a packed bed and ensure stable operation over time. In conventional LC columns with an inner diameter of 2.1 or 4.6 mm, for example, frits are typically made out of stainless steel or titanium particles sintered together, or screens, meshes and composites, that are mechanically press-fit into the ends of the column. In columns made out of fused silica capillaries, with inner diameters 75 to 150 microns, the frits are typically made with chemical means by dipping the end of the capillary into a polymeric solution that locks the ends of the column in place when it cures. Another method for capillary columns is to burn a section of the capillary to fuse the particles together.

Frits can be made before or after packing. For example, it is possible to frit the outlet of the column and pack against it, then frit the inlet. Alternatively, a temporary external frit can be placed against the outlet of the column during packing, for example in the outlet capillary that carries the slurry liquid to waste, and removed after packing is complete, after which permanent fits are made on the capillary column at the outlet and possibly the inlet.

In planar microfluidic devices for LC applications, there can be several possible methods for fabricating frits. The geometry of such a device is shown schematically in FIG. 1. In this illustration, the device 100 is made by joining two layers. The top layer 101 contains two through-holes, or vias, 102. The lower layer 103 contains a groove 104. After alignment and joining of the two layers, a hermetically sealed channel is formed. Fittings are attached to the device 100 in order to make fluid connections to the vias 102. Particles dispersed in a slurry flow through the inlet via into the channel and out of the outlet via. A frit, either temporary or permanent, must be placed in the outlet via or after the outlet via in order to retain particles. If the frit is temporary and removed after packing is complete, a permanent outlet frit is made after packing. This frit must be capable of withstanding substantial force applied in subsequent operation without moving or rupturing. Frit motion would likely cause degradation of the column performance. Frit rupture would typically cause complete failure of the column. Typically, a permanent inlet frit is also created so that the packed bed is firmly locked into place.

A first class of frits for microfluidic devices uses chemical solutions such as silicate. A drop is placed at the vias and allowed to cure, upon which the polymeric solution creates bridges between the particles and physically locks them in place. Another class of frits for microfluidic devices employs frits that are micro-machined along with other features of the device, such as channels and vias. In prior art techniques, the physical restriction that achieves retention of the particles inside the microfluidic device is an integral component of the device and is fabricated along with it. As such, the retaining device in those situations is fabricated prior to packing the particles into the microfluidic columns. Therefore, those retaining devices can only be fabricated at the column outlet.

Mechanical frits, typically made out of stainless steel or titanium particles compacted and sintered together, are a standard method for creating retaining structures in traditional LC columns. Typically, in a traditional column (see FIG. 2), made from a stainless steel tube 200, a first frit ring assembly 201, consisting of a frit 203 inside a frit ring 202, is placed at the outlet end of the tube 200 and maintained in place by an outlet end nut 204. Particles in a slurry are packed against this frit. A second frit assembly 205 is placed against the inlet of the tube 200 after packing and maintained in place using the inlet end nut 206.

BRIEF DESCRIPTION OF THE DRAWINGS

Reference will now be made to the accompanying drawings, which are not necessarily drawn to scale, and wherein:

FIGS. 3B and 3C depict a cross section of the fluidic device of FIG. 3A during various stages of insertion of porous media into a cavity of the fluidic device;

FIGS. 4A and 4B depict a cross section of another illustrative embodiment of a microfluidic device during pre and post insertion of porous media into a cavity of the fluidic device;

FIGS. 7A and 7B depict a cross section of another illustrative embodiment of a fluidic device during pre and post insertion of porous media into a cavity of the fluidic device;

FIGS. 8A and 8B depict a cross section of yet another illustrative embodiment of a fluidic device during pre and post insertion of porous media into a cavity of the fluidic device;

FIGS. 9A and 9B depict a cross section of yet another illustrative embodiment of a fluidic device during pre and post insertion of porous media into a cavity of the fluidic device;

FIGS. 10A-10H depict cross sections of illustrative embodiments of a fluidic device together with cross sections of embodiments of a porous media insertion tool;

FIGS. 11A-11C depict a cross section of yet another illustrative embodiment of a fluidic device during pre and post insertion of porous media into a cavity of the fluidic device;

FIGS. 12A-12C depict a cross section of yet another illustrative embodiment of a fluidic device during pre and post insertion of porous media into a cavity of the fluidic device;

FIGS. 14A-14C depict cross sections of another illustrative embodiment of pre-formed frit during preforming to post insertion;

DETAILED DESCRIPTION

Figure 1:
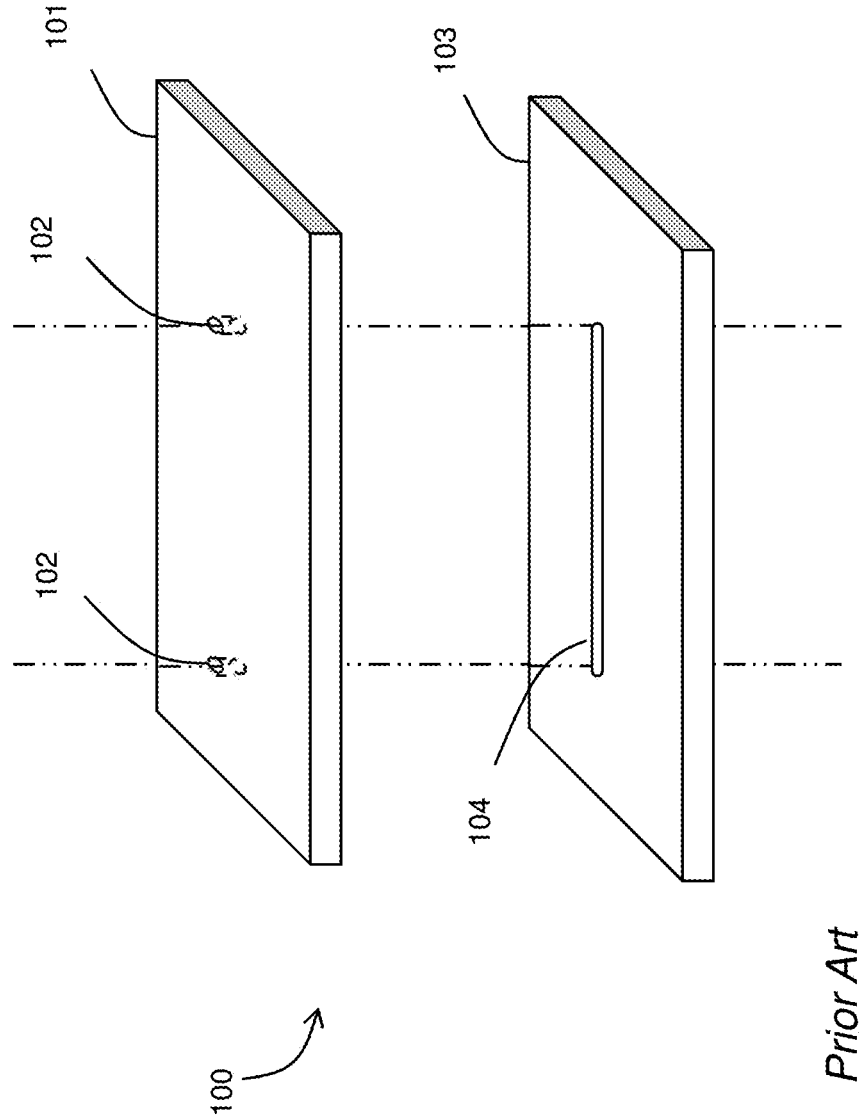
FIG. 1 depicts an exploded view of a prior art planar microfluidic device.

The subject disclosure describes, among other things, illustrative embodiments of a porous medium configured for mechanical insertion into a fluidic device, such as a planar microfluidic device. The porous medium can have an initial porosity profile that remains unchanged or is transformed to a target porosity profile. The porous medium can be used in combination with a fluidic device, for example, to restrict, alter or otherwise control a flow of fluid within the device. The porosity profile can be uniform or non-uniform, depending upon an intended application. Applications of the subject disclosure can include, without limitation, frits, filters and flow restrictors.

One embodiment of the subject disclosure includes a process that obtains a porous medium comprising a porous material having a first shape and an initial porosity profile. The porous medium is engaged with a cavity in a fluidic device, wherein the cavity is in fluid communication with a channel of the fluidic device. The engaging of the porous medium with the cavity causes the first shape of the porous material to be adjusted to a second shape resulting in the initial porosity profile being adjusted to a target porosity profile.

Another embodiment of the subject disclosure includes a planar microfluidic device having a first planar member defining a microfluidic channel. The microfluidic channel has a channel diameter to accommodate a fluid flow. The planar microfluidic device includes a second planar member defining a cavity. The cavity has an open end in proximity to a surface of the second planar member, wherein the cavity has a dimension that is substantially greater than the channel diameter. The cavity is in fluid communication with the channel when the first planar member and the second planar member are joined together in a stacked arrangement. A pre-formed porous medium comprising a porous material having a porosity profile disposed within the cavity. The fluid flow is directed through at least a portion of the pre-formed porous medium.

Yet another embodiment of the subject disclosure includes a process that obtains a porous medium comprising a porous material having a non-uniform porosity profile. The porous medium is engaged with a cavity in a fluidic device, wherein the cavity is in fluid communication with a channel of the fluidic device. The non-uniform porosity profile is selected for directing a fluid flow through the porous medium in proximity to an opening of the channel to reduce fluid diffusion.

Transformation of the porous member from the initial porosity profile to the target porosity profile can be accomplished by a change in shape of the porous member. In particular, a change in shape introduces a corresponding change in volume. Reducing a volume of the porous member will generally reduce the porosity of the porous member by reducing an open or void volume relative to a volume of particulate, fibrous, woven or other material forming a supporting structure of the porous member.

A porosity profile refers to a relative measure of porosity across the porous member. A uniform porosity profile exhibits a constant or uniform porosity value across the porous member, whereas a non-uniform porosity profile exhibits a varying porosity value across the porous member. An initial porosity profile of the porous member can be uniform or non-uniform. Likewise, a target porosity profile can also be uniform or non-uniform, regardless of the initial porosity profile. Based on the embodiments of the subject disclosure, a porous member having an initial porosity profile can be transformed to a target porosity profile for achieving a desirable result that may relate to directivity of fluid flow, filtering, flow restriction, or any combination thereof.

Figure 3A:
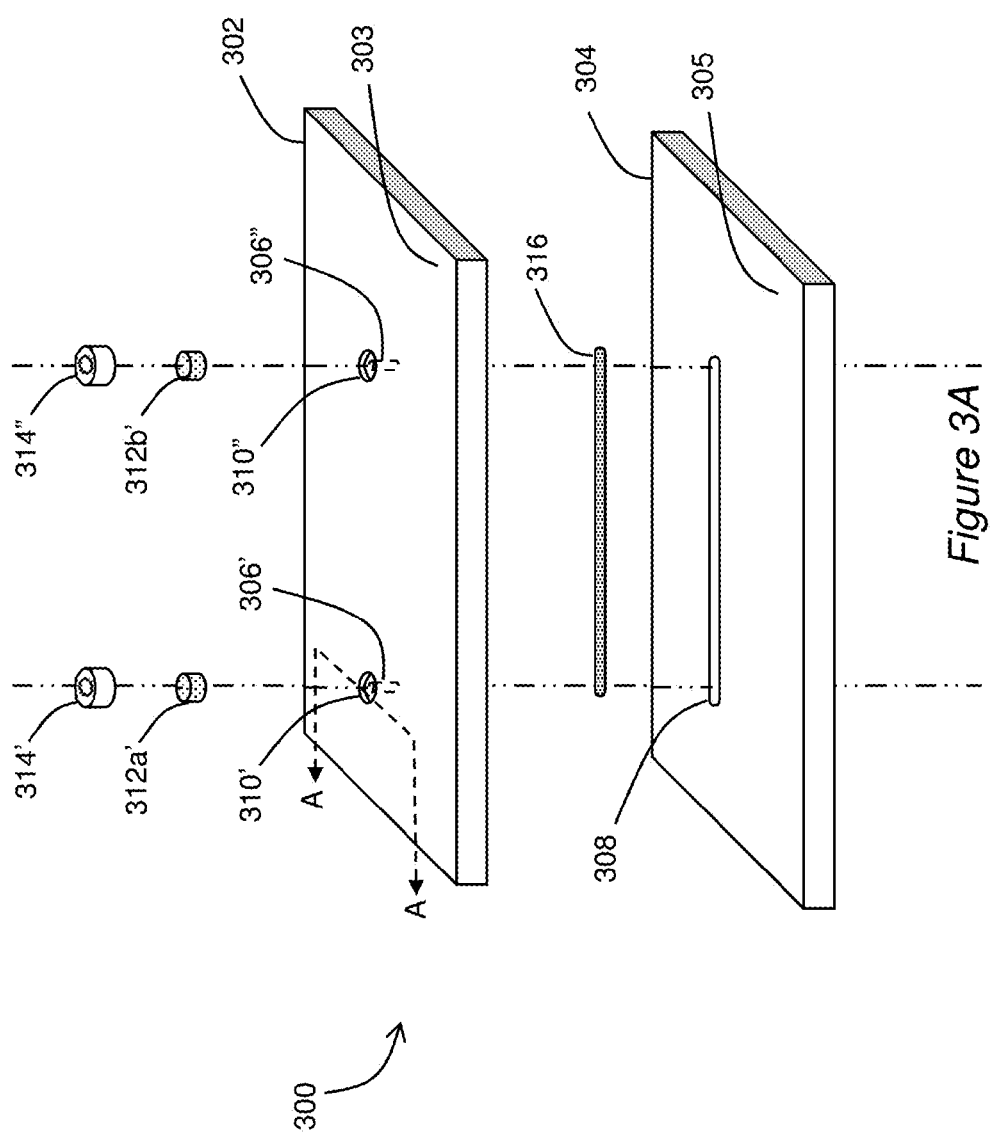
FIG. 3A depicts an exploded view of an illustrative embodiment of a planar microfluidic device.

FIG. 3A depicts an exploded view of an illustrative embodiment of a planar fluidic device 300 including an LC column bounded at its input and output by frits formed according to the techniques disclosed herein. For example, the frits can be mechanically inserted into cavities formed in a surface of the device. The frits can be fabricated from porous media having a uniform porosity profile that is reshaped before, during or after the insertion process. The resulting reshaping adjusts the uniform porosity profile to a target porosity profile. The target porosity profile can, for example, offer a greater porosity in a central region aligned with an axis of a via, which is in fluid communication with the column, while offering a lesser porosity in an outer region away from an axis of the via. Such a target porosity profile is advantageous in LC applications in that it tends to reduce fluid diffusion which can cause dispersion in detection peaks presented by analysis equipment.

The fluidic device 300 includes an upper layer 302 and a lower layer 304. The upper layer 302 contains two through-holes, or vias, 306', 306" (generally 306), while the lower layer 304, contains a groove, furrow or channel, 308. The groove 308 is dimensioned to extend between the two vias 306 when the upper and lower layers 302, 304 are aligned for joining. The vias 306 form fluid access (ingress, egress) ports along the top surface of the device 300. In some embodiments, a channel (not shown) may extend to an edge of the bonded part, defining another fluid access port along an edge.

The stacked layers 302 and 304 can be joined by diffusion-bonding, so that the groove 308 and a bottom surface of the upper layer 302 become a fluid channel (e.g., a separation channel) capable of holding fluids hermetically under high hydraulic pressures. It is understood that in at least some embodiments, the bottom surface of the upper layer 302 includes a complementary groove that aligns with the groove of the lower layer 304, or with a flat surface of the lower layer 304.

A fluid, such as a liquid, a gas, or a combination of a liquid and a gas introduced at a first one of the vias 306', travels through the first via 306' and enters one end of the fluid conduit. Without obstruction, the fluid is free to flow through the conduit towards the second via 306". The fluid can exit the device 300 by way of the second via 306". It is understood that alternate configurations of one or more channels 308, vias 306 and the like can be used alone or in combination with other features to move, mix, separate and/or otherwise process fluid samples. The cross-sections of the channel(s) 308 can have semi-circular or semi-elliptical shapes, e.g., when chemical or electrochemical machining are used to form the grooves, and rectangular shapes, e.g., when milling is used, with typical width and height of 50-500 micrometers.

An embodiment of a packing material 316 is shown having a form that conforms to the dimensions and shape of the channel 308. The packing material 316 can be introduced in the form of a powder or slurry that takes on the form of the channel 308 after being packed into the channel 308 during formation of the LC column.

The upper layer 302 includes two open-ended cavities 310', 310" (generally 310) aligned with the two vias 306, such that each via 306 is in fluid communication with a respective one of the open-ended cavities 310. In particular, a cross section of the open-ended cavity 310 taken in a plane perpendicular to via axis has an open area that is substantially greater than a cross-section area of the via 306. By way of non-limiting example, a tubular via 306 can have a diameter between about 50 and 200 microns, whereas a cylindrical open-ended cavity 310 can have a diameter of about 2-3 mm or more. Beneficially, such relatively wide, open-ended cavities accommodate frits having a size (e.g., 2-3 mm) that facilitates mechanical insertion. Without limitation, diameters of other channels (not shown) in fluid communication with the via 306' can range from about 0.5 mm to about 1 mm.

The example device 300 includes two frits 312a', 312b' (generally 312) positioned at respective ends of the channel 308 (column) to hold packed particles of the packing material 316 in place, while also allowing a fluid to flow through the packed column. In use, an inlet tube (not shown) is connected between a first one of the vias 306' of the planar fluidic chemical separation device 300 and an injection valve and pump (not shown). The pump delivers a flow of mobile phase at a specified flow rate, which is typically constant throughout a separation. The injection valve injects into the mobile phase a plug or band of the sample. This band travels with the mobile phase to the separation channel 308, where its components are separated. An outlet tube (also not shown), which is connected to the other one of the vias 306" at the opposite end of the separation channel 308, transports the separated components to a detector (e.g., a UV detector or mass spectrometer), which, in turn, may be connected to a computer data station for recording an electrical signal from the detector and generating a chromatogram—see FIG. 14. The inlet and/or outlet tubes can be formed as part of the same fluidic device, e.g., a lab on a chip, as part of another fluidic device positioned in fluid communication with the device 300, or as part of an interconnecting fluid network, e.g., providing a fitting or suitable fluid port or coupler to promote a fluid-tight transfer of fluid to and/or from the device 300.

Fittings 314', 314" can be attached to the device 300 in order to make fluid connections to the vias 306. Particles dispersed in a slurry can be introduced into the channel 308 by way of a fluid flow through an inlet via 306' into the channel 308 and out of an outlet via 306". A frit 312, either temporary or permanent, is placed in the outlet via 306" or after the outlet via 306" in order to retain the particles within the channel 308 of the device 300. If the frit 312 is temporary and removed after packing is complete, a permanent outlet frit 312b' can be made after packing. The frit 312 must be capable of withstanding substantial force applied in subsequent operation without moving or rupturing. The force results from a pressure differential developed across the frit 312. Typically, a permanent inlet frit 312a' is also created so that the packed bed 316 is firmly locked into place.

FIG. 3B illustrates a cross section of the fluidic device 300 taken along section A-A (FIG. 3A). The open-ended cavity 310' is open at one end that defines a perimeter 319' along an exposed top surface 303 of the upper layer 302. The cavity 310' includes an opposing closed end that is separated from the open end by a side wall 318'. The closed end includes a floor surface 317' open to a proximal end of the via 306' by way of an orifice, or fluid port 316'. In the illustrative example, the floor surface 317' is substantially flat and parallel to the exposed top surface 303, and offset from the exposed top surface 303 by a height h.

Although the examples disclosed herein generally reflect a single via centered with respect to the cavity, it is understood that the via can be located without restriction at an edge of the cavity floor. More generally, the via can be located at any position along an interior surface of the cavity, including a side wall. It is also understood that a single fitted cavity can be in fluid communication with more than one via, capillary or fluid channel, such that the target porosity profile provides a uniform fluid flow or a non-uniform flow to the multiple vias.

A porous media member or plug 312a' is shown in axial alignment with the via 306' and positioned above the open end of the open-ended cavity 310'. The porous media plug 312a' has a plug-width dimension, or diameter of $d_2$. The open ended cavity 310' can provide a cavity width dimension or diameter of about W, possibly being slightly less to promote frictional engagement of the porous media plug 312a' when pressed into the open end of the cavity 310'. In the illustrative example, the width or diameter $d_2$ of the porous media plug 312a' is substantially greater than a width or diameter $d_1$ of the via 306'. The width or diameter of the via $d_1$ is determined or otherwise selected according to the particular fluidic process.

The porous media plug 312a' has a pre-insertion thickness t measured in an axial direction with respect to an axis of the via 306'. Upon insertion, a force, indicated by the insertion force arrow, presses the porous media plug 312a' into the open end of the cavity 310'. In some applications, the thickness t of the pre-insertion porous media plug 312a' is approximately equal to a height or depth h of the open-ended cavity 310'. The plug 312a' can be inserted into the cavity 310' partially, such that a portion of the plug 312a' remains exposed above the top surface. In other instances, the plug 312a' can be inserted into the cavity 310' such that the plug 312a' is completely contained within the cavity. After insertion, a top surface of the plug 312a' can be substantially aligned with the top surface 303 of the device 300, as shown in FIG. 3C. In other embodiments, the top surface of the plug 312a' can be depressed, recessed or otherwise positioned within the cavity and below the exposed top surface 303.

Depending on a particular application, fluid can be introduced into the via 306' from the exposed top portion 303 of the fluidic device 300. In some applications, to facilitate a fluid coupling, the device includes a fluid port. The fluid port or coupler can be attached to the exposed top surface 303. In the illustrative example, the fluid port includes a circumferential collar or fitting 314' having base adapted for attachment to the top surface 303, a wall portion extending in an axial direction away from the base and a central opening defined by the wall portion. The central opening is sized and shaped to accept a fluid fitting 320 (shown in phantom). The fluid fitting 320 can include a fluid lumen to promote transfer of fluid to and/or from the fluidic device 300.

It is understood that in some applications, the thickness of the porous media plug 312' is reduced upon compression before, during and/or after insertion into the cavity 310'. A target porosity profile can be obtained based on an initial porosity profile of the porous media plug 312 being changed by any suitable means, including mechanically, e.g., by compression to reduce a thickness or thermally, e.g., by melting or otherwise selectively fusing or occluding at least some of the pores. In the illustration of FIG. 3C, the original porosity profile of the frit is uniform. The compression of the frit into the cavity results in a target porosity profile. The target porosity profile can also be uniform since the shape of the frit remains much the same. When t is greater than h, however, the target porosity has a lower uniform porosity than the original porosity profile due to the compression of the frit into the cavity. When t is the same or less than h, the target porosity profile can be approximately the same as the original porosity profile.

FIGS. 4A and 4B depict a cross section of another illustrative embodiment of a fluidic device during pre and post insertion of a porous medium into a cavity of the fluidic device, in which a target porosity is obtained according to a shape of the cavity. Namely, the target porosity is obtained according to a shape of a floor or base wall of the cavity. In this embodiment, the shape of a porous medium 412' is adjusted from a pre-insertion shape, e.g., a flat disc, to an insertion shape, a conical disc, according to a shape of the cavity 410. Namely, the open ended cavity 410 includes a sloped floor portion 417 posing different heights to the exposed surface 403 of the device 400. In this example, a deepest portion of the cavity 410 is located in an immediate vicinity of an orifice 416 that opens to a proximal end of a fluid channel, or via. The compressed frit 412" has an outer region 424 that is compressed to a greater degree than a central region 426. According to the principals disclosed herein, porosity of the outer region 424 is reduced, whereas porosity of the central region 426 can remain unchanged, i.e., no compression, or change to a lesser degree than the outer region 424. Beneficially, a reduced porosity in the outer regions tends to contain, restrict or otherwise focus a fluid flow of the frit 312" to the central region, which is aligned with the orifice 416 and has a greater porosity and which can help reduce diffusion in chromatography applications. It is understood that such a non-uniform target porosity profile, promoting concentration of a fluid flow to a central region, can be obtained by compressing or otherwise varying a shape of a porous medium having an initially uniform porosity profile.

Figure 5A:
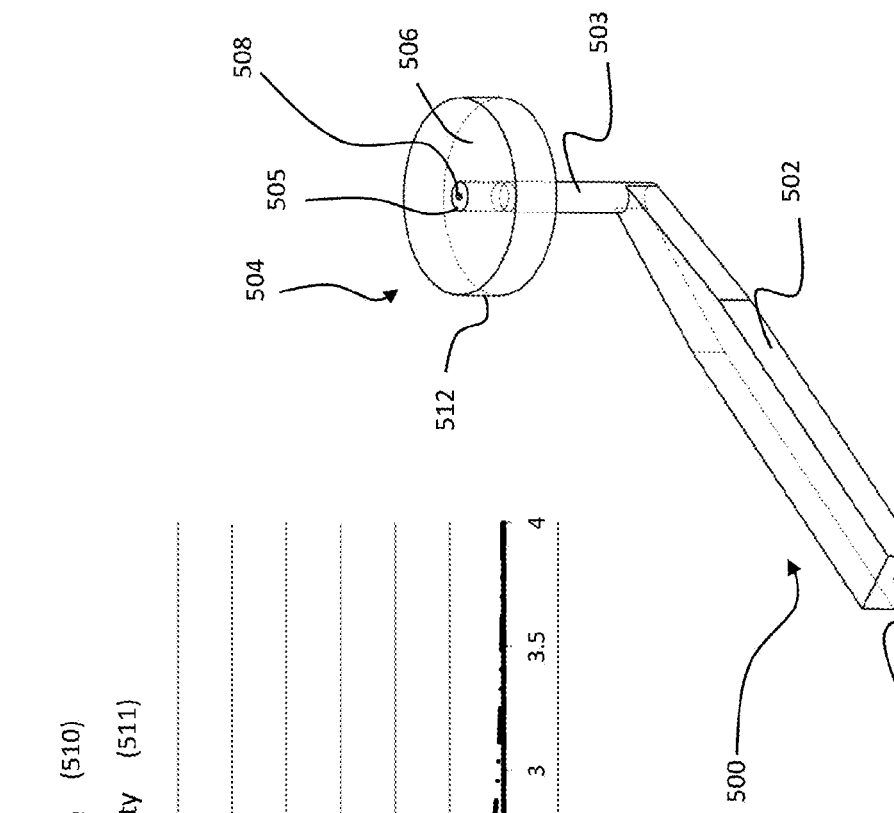
FIG. 5A depicts a computer model of a portion of a fluidic device including porous media modified according to the techniques disclosed herein.

FIG. 5A illustrates a model of a portion of a planar microfluidic device 500. The modeled device 500 includes a relatively short section of a channel 502 in fluid communication with one end of a via 503. The device 500 also includes a frit 504 in fluid communication with an opposing end of the via 503. The channel 502 has width of 0.35 mm and height of 0.2 mm (e.g., for an equivalent diameter of about 0.3 mm). The via 503 has a cross-sectional diameter of 0.15 mm and an axial length, or height of 0.75 mm. The frit 504 has a diameter of 1.0 mm and a height or thickness of 0.25 mm.

The example frit 504 consists of two distinguishable regions or parts: an inner or center region 505 about a central axis aligned with a longitudinal axis of the via 503 and an outer or edge region 506 extending between the center region 505 and an outer perimeter 512. Porosities of the center region 505 and the edge region 506 can be different, resulting in a non-uniform porosity profile, according to the techniques disclosed herein. In the illustrative example, the center region 505 of the frit 504 has a diameter of about 0.15 mm, which corresponds to a cross section dimension of the via 503. It is envisioned that in other embodiments the diameter of the center region 505 can be greater than or less than the cross-sectional diameter of the via and/or that the frit 504 can abut the channel 502, e.g., without the via 503.

Figure 5B:
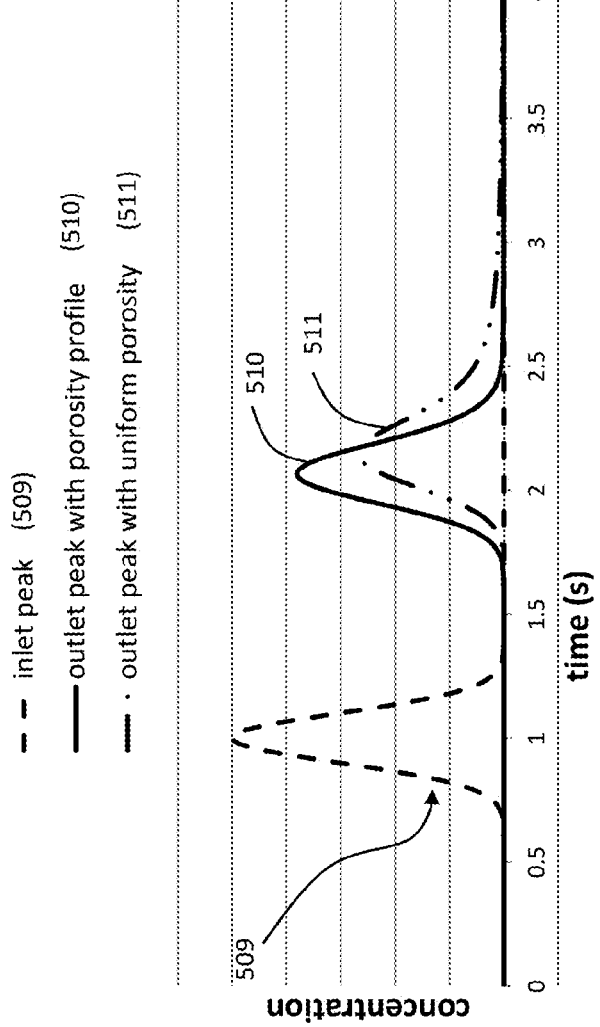
FIG. 5B depicts simulation results of band-broadening performance of the modeled device of FIG. 5A.

A simulation of performance of the modeled device 500 was performed to qualitatively and quantitatively to demonstrate expected performance of the device 500. A graphical illustration of the simulation results is illustrated in FIG. 5B. In the example simulation, an inlet peak 509 represents a concentration of a fluid sample introduced at an input end 507 of the channel 502 with respect to time. In a liquid chromatography application, the fluid would represent a sample under investigation injected within a liquid mobile phase according to the inlet peak 509. Volumes of the sample fluid can vary, e.g., being about 1 microliter.

In the illustrative example, the inlet peak 509 corresponds to a Gaussian distribution. The sample travels downstream, through the channel 502, through the via 503 and through the frit 504 before exiting the device 500. According to the simulation, an outlet concentration of the sample, or outlet peak, was determined at an outlet of the device 500. In particular, the outlet corresponds to a small surface 508 at an output, or downstream side of the frit 504. Accordingly, the outlet peak reflects contributions of the frit 504.

A change in shape between the outlet peak and the inlet peak 509 indicates a degree of dispersion, or peak broadening. Any measure of the peaks can be used for the purpose of comparison. In the illustrative examples, peak broadening is determined according to a measure of the variance of each peak. The simulation was performed for the same basic geometry of the device 500, but with different physical properties attributed to the frit 504. In a first scenario, the frit edge 506 and the frit center 505 have the same porosity value of 32%. In a second scenario, a porosity of the frit edge 506 was 0.1%, which was much smaller than the porosity of the frit center 505, which was 32%. A first outlet peak 511 illustrates the sample concentration versus time determined at the outlet 508 for the first scenario having a uniform porosity profile. Likewise, a second outlet peak 510 illustrates the sample concentration versus time determined at the outlet 508 for the second scenario having a non-uniform porosity profile. It is apparent that the first outlet peak 511 representing a concentration of the sample exiting the frit 504 having a uniform porosity profile is significantly broader than the second outlet peak 512 representing a concentration of the sample exiting of the frit 504 having a non-uniform porosity profile, according to the invention.

Figure 6:
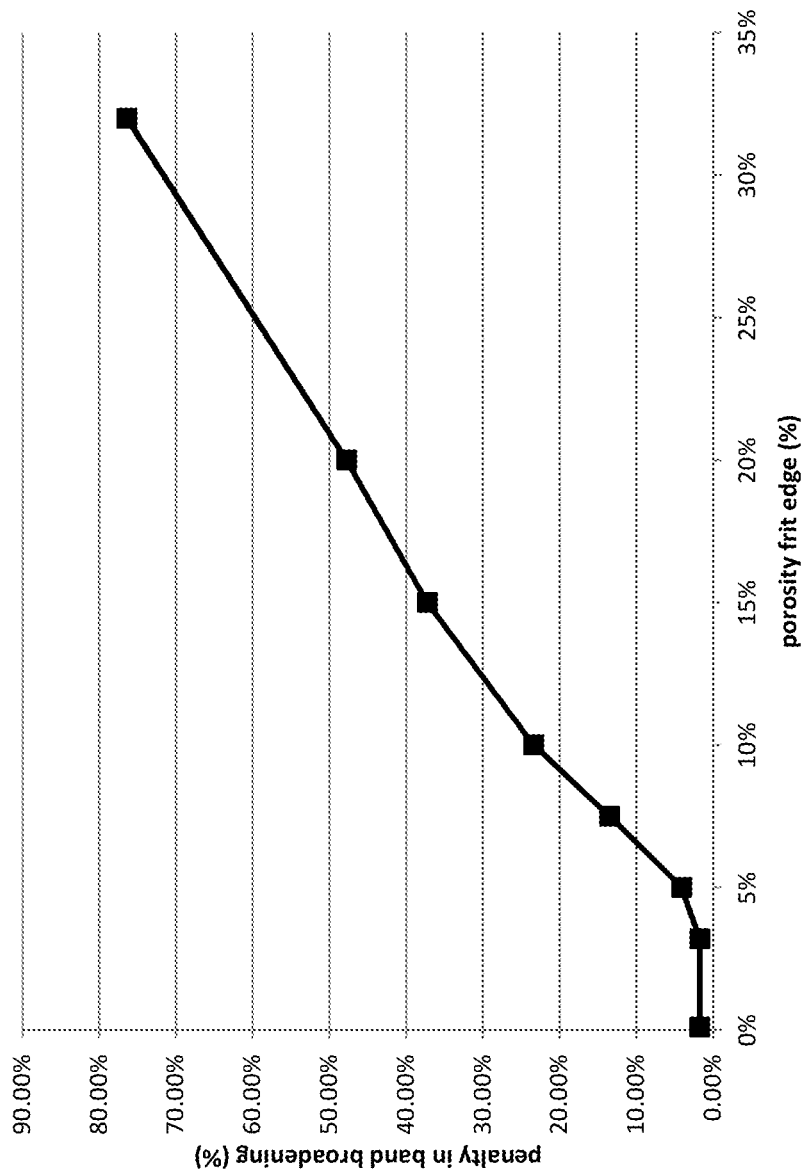
FIG. 6 depicts simulation results of band-broadening performance of the model of FIG. 5A according to a range of different porosity profiles.

Peak-broadening performance of frits 504 having a range of porosity profiles are illustrated further in FIG. 6. The figure is the result of a series of computer simulations, which considered a 10 cm long, 0.3 mm diameter microfluidic column with 0.75 mm long, 0.15 mm diameter vias, and an outlet frit of length 0.25 mm and diameter 1.0 mm. As in FIGS. 5A and 5B, the frit 504 had a center portion 505 of diameter 0.15 mm with a porosity of 32%. In the series of simulations, the porosity of the edge 506 of the frit 504 was varied between about 0 and 32%.

It is generally preferable, at least in liquid chromatography applications, to introduce as little peak broadening as possible. The resulting plot of FIG. 6 suggests a "penalty" or increase in peak broadening, measured by the plate height, a very common metric of chromatographic performance, as a function of the porosity of the edge of the frit. When the frit has uniform porosity profile, i.e., for a frit edge porosity value of 32%, the penalty in peak broadening is greater than 70%, which is generally unacceptably high for liquid chromatography applications. When the frit edge porosity value is under 5%, the penalty is less than 10%, which is generally acceptable for such applications. The results illustrate that the devices and techniques disclosed herein allow for the use of a relatively large frit with little or no penalty in band broadening. Namely, a frit that is substantially larger than a cross-sectional size of an adjacent channel or via can be mechanically introduced into (and/or removed from) a microfluidic device, while providing little or no contribution to peak broadening of a sample processed by the device.

FIGS. 7A and 7B depict a cross section of another illustrative embodiment of a fluidic device during pre and post insertion of a porous media plug 712' into a cavity 710 of the fluidic device 700. Once again, a target porosity is obtained according to a shape of a floor or base wall 717 of the cavity, a significant difference being cavity features 722 to promote retention of the plug 712' within the cavity, even in the presence of substantial pressure differentials across the plug 712'. In this embodiment, a shape of the porous medium 712' is adjusted from a pre-insertion shape, e.g., a flat disc, to an insertion shape, a conical disc, according to a shape of the cavity 710. Once again, a porosity of a central region 726 of the frit 712" is greater than a compressed porosity of an outer region 724. This configuration promotes or otherwise constrains a passage of fluid through the frit 712" to the central region 726 of the frit 712".

In this example, the deepest portion of the cavity 710, adjacent to the floor wall 717 includes a depression, ridge or groove 722. In some embodiments, the groove 722 extends peripherally about the side wall 718. In other embodiments, the groove can extend for a portion, e.g., an arc length, that is less than or greater than the perimeter of the side wall 718. For example, the groove 722 can comprise a helical groove. In other embodiments more than one groove can be provided in the side wall. The grooves can be located at various heights and with various configurations without limitation. In the presence of an insertion force, e.g., provided during press-fitting the plug 712' into the cavity 710, a portion of the porous medium extends into the groove 722. Any such portion of the porous medium that extends or otherwise protrudes into the groove 722 can promote retention of the frit 712" within the cavity 710 by increasing performance of the resulting interference fit.

It is worth noting here that differences in porosity profiles for various embodiments are illustrated with dashed lines and/or shading to signify different regions having different porosity values of a non-uniform porosity profile. It should be understood that the transitions may or may not be abrupt as suggested by the dashed lines, for example, varying in a continuous and/or discontinuous manner across the porous device. Such variations can be uniform or non-uniform along an axial direction. Similarly, the transitions may be linear, piecewise linear, curved, nonlinear and so forth.

FIGS. 8A and 8B depict a cross section of another illustrative embodiment of a fluidic device 800 during pre and post insertion of a porous media plug 812' into an open-ended cavity 810. This example demonstrates a target porosity profile obtained according to compression of the plug 812' into the cavity 810 and at least partially into an open end of a via 816. In this embodiment, the shape of the porous medium, or plug 812' is adjusted from a pre-insertion shape, e.g., a flat disc, to a post insertion shape, e.g., a disc having a protrusion 825 along one side. The protrusion 825 extends below a floor wall 817 of the cavity 810 and into the open end of the via 816 in fluid communication with the cavity 810. The shape of the plug 812' is adjusted according to a configuration of the floor wall 817 in combination with the open end of the via 816. In this instance, the open cavity 810 is a right circular cylindrical cavity 810.

In the presence of an insertion force, e.g., provided during press-fitting the plug 812' into the cavity 810, the plug 812' is transformed into a compressed plug 812" having an outer or edge region 824 determined according to compression of the plug 812' against an adjacent surface of the floor wall 817. The compressed plug 812" also has an inner or central region 826 positioned over the open end of the via 816. The inner region 826 is aligned with the protrusion 825 and extends across the thickness of the compressed plug 812". The plug 812' is allowed to expand or otherwise extend at least partially into the open end of the via 816 during compression of the outer region 824, resulting in the protrusion 825. The resulting frit 812" has a porosity profile in which a porosity of the inner region 826 that is greater (more porous) than a porosity of the outer region 824. In some embodiments, the porosity of the outer region 824 approaches zero. Such configurations promote or otherwise constrain a passage of fluid through the frit 812" to the central region 826 of the frit 812". A shape and depth of the protrusion 825 can be controlled according to various features, including one or more of the particular material of the porous medium 812', a diameter of the open end of the via 816, an extent of compression, a shape of the floor wall 817 (e.g., non-planar), and so forth.

FIGS. 9A and 9B depict a cross section of an illustrative embodiment of a variation of the fluidic device illustrated in FIGS. 8A and 8B. The device 900 includes an open-ended cavity 910 having a floor wall 917 that opens to an open end of a via 916 by way of a counter bore 918. The counter bore 918 is axially aligned with the via 916 extends between an opening in the floor wall 917 and the open end of a via 916. A frit 912' is inserted into an open end of the cavity 910 and compressed against the floor wall 917 to form a compressed frit 912". The insertion and/or compression force urges a portion of an inner region 926 of the frit 912" at least partially into the counter bore 918 forming a protrusion 925. In the illustrative example, the protrusion 925 extends into the counter bore 918 and up to the open end of the via 916. Once again, the resulting compressed frit 912" has a porosity profile in which a porosity of the inner region 926 is greater (more porous) than a porosity of the outer region 924. This configuration promotes or otherwise constrains a passage of fluid through the compressed frit 912" to the inner or central region 926 which is aligned with the via 916. It is understood that in at least some embodiments, a portion of the protrusion 925 can extend beyond the counter bore 918 and at least partially into the open end of the via 916 (not shown). Such a configuration can result in a porosity profile having a graded or stepped change between the outer and inner regions 924, 926.

The preceding embodiments depict the use of a shape of a device cavity for adjusting a shape of a porous medium during insertion of the porous medium into the cavity. It is understood that in at least some applications, the shape of the porous medium can be adjusted by a rod, piston, punch or mantle used to apply a press-fitting force, or a similar device providing compression after the porous medium has been inserted into a cavity.

FIGS. 10A-10H depict cross sections of illustrative embodiments of a fluidic device 1000 include a substrate 1002 having an open-ended cavity 1010 with an open end open to a surface of the device 1000 and an opposing closed wall. The closed wall includes an orifice or port coupled to a proximal end of a fluid port or via 1009. Also shown is a cross section of a porous media plug 1012b in juxtaposition between a punch 1004 and the cavity 1010. In this embodiment, the shape of the porous medium 1012*b* is adjusted from a pre-insertion shape, e.g., a flat disc, to a post-insertion shape according to a shape of a facing end of the punch. Instead of being adjusted by the floor wall 417, 717 (FIGS. 4B, 7B), the shape is adjusted by a configuration of a facing end 1008 of the punch.

With respect to FIGS. 10A-10B, a target porosity profile is obtained by a uniform re-shaping or compression of the porous media plug 1012*b* according to a mantle surface 1008 of the punch 1004. A uniform target porosity profile is generally obtained by uniform compression of a uniform initial porosity profile throughout the region 1013*b*. The facing end 1008 of the punch 1004 provides a flat surface to provide a uniform compressive force across the surface during compression of the porous media plug 1012*b* into the open-ended cavity 1010. Depending upon the radial diameter of the punch 1004, either the entire porous media plug 1012*b* is compressed uniformly, or a central region is compressed. For example, to avoid causing a higher porosity at the edges of the frits, which can result in an accumulation of fluid on the side walls of the cavity, and consequently cause fluid diffusion, the radial diameter of the punch 1004 can be configured to be equal or greater than the radial diameter of the frit so that all surfaces of the frit are compressed equally, and the resulting target porosity profile is uniform. The same can be said for any of the other embodiments disclosed herein.

With respect to FIGS. 10C-10D, a target porosity profile can be obtained by a non-uniform re-shaping or compression of the porous media 1012*d* according to a facing surface or mantle 1018 of the punch 1014. In particular, a target porosity profile can be obtained in a compressed frit 1012*d'* that has a stepped porosity profile offering a relatively greater porosity in a central region 1013*d* when compared to an outer region 1016*d*. Namely, a facing end 1018 of the punch 1014 can include a planar recessed area 1019, presenting a planar surface of the recessed area that is parallel to the surface of the device 1000. In the illustrative embodiment, the recessed area is located in an interior region that is axially aligned with an axis of the via 1006. In some embodiments, the punch 1014 includes a shoulder 1015. The shoulder 1015 can be sized and spaced to abut the surface of the device 1000 upon insertion to control a depth of insertion and/or compression. It is conceivable that such a shoulder 1015 could be arranged along another part of the punch 1004 or interconnected machinery (not shown) to similarly control a depth of insertion/compression during use. Beneficially, a resulting frit 1012*d'* formed from the porous media plug 1012*d* after compressed will have a central region 1013*d* with a greater porosity than an outer region 1016*d* away from the axis of the via 1006.

Although a top surface of the compressed frit 1012*d'* is illustrated in cross section as being non-planar, with at least a portion of the frit 1012*d'* extending above and/or below a surface 1003 of the device 1000, it is understood that in at least some embodiments, the compressed frit 1012*d'* can be flush with the surface 1003 of the device 1000. For example, the dimensions and/or compression can be controlled such that the no top surface portions of the compressed frit remain recessed below the surface 1003 of the device 1000. Any portions of the compressed frit 1012*d'* extending above the surface 1003 of the device 1000 can be removed, e.g., by abrasive techniques, polishing, milling and the like, such that an exposed surface of the compressed frit 1012*d'* is flush with the top surface 1003 of the device 1000. Such techniques can be applied alone or in combination with any of the devices and techniques disclosed herein.

Figures 10E, 10F, 10G, 10H:
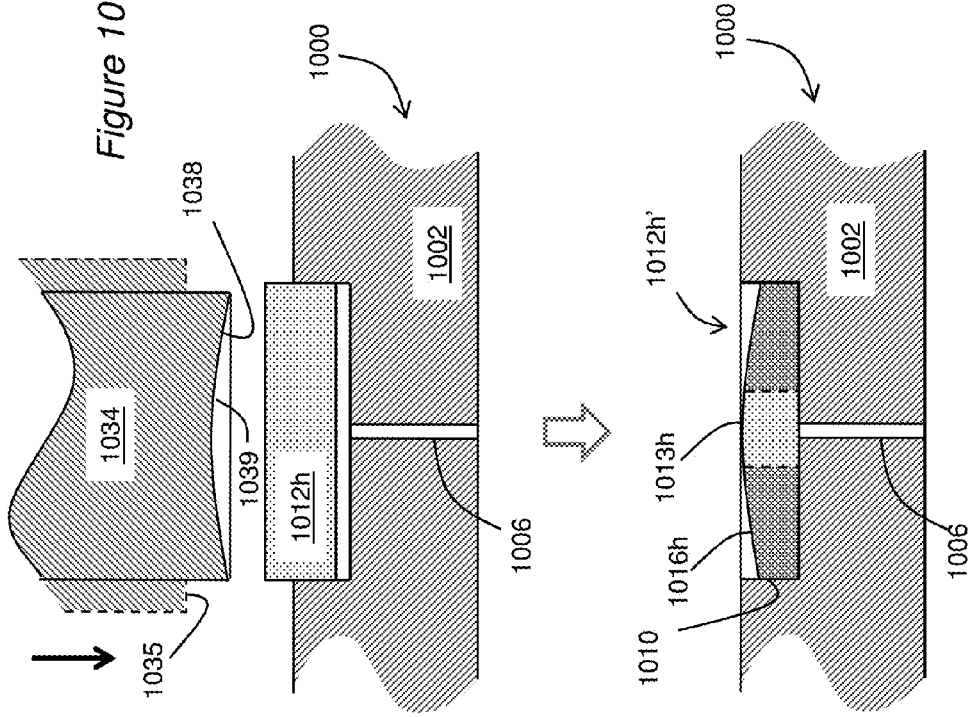

With respect to FIGS. 10E-10F, a target porosity profile is obtained by a non-uniform re-shaping or compression of the porous media 1012*f* according to a mantle surface 1028 of the punch 1024. In particular, the target porosity profile has a sloped porosity profile offering a relatively greater porosity in a central region 1013*f* when compared to an outer region 1016*f*. Namely, a facing end 1028 of the punch 1024 includes a conical recessed area 1029, presenting a concave, conical surface at the punch end 1028. In the illustrative embodiment, the recessed area is more recessed along an interior region that is axially aligned with an axis of the via 1006. In some embodiments, the punch 1024 also includes a shoulder 1025 that can be used to facilitate compression and/or insertion to a controlled depth. Beneficially, a resulting frit 1012*f'* formed form the porous media plug 1012 after compressed will have a central region 1013*f* with a greater porosity than an outer region 1016*f* away from the axis of the via 1006.

With respect to FIGS. 10G-10H, a target porosity profile is obtained by a non-uniform re-shaping or compression of the porous media 1012*h* according to a mantle surface 1038 of the punch 1034. In particular, the target porosity profile has a curved porosity profile offering a relatively greater porosity in a central region 1013*h* when compared to an outer region 1016*h*. Namely, a facing end 1038 of the punch 1034 includes a curved recessed area 1039, presenting a concave, curved surface at the punch end 1038. In the illustrative embodiment, the recessed area is more recessed along an interior region that is axially aligned with an axis of the via 1006. In some embodiments, the punch 1034 includes a shoulder 1035 that can be used to facilitate compression and/or insertion of the porous medium to a controlled depth. Beneficially, a resulting frit 1012*h'* formed form the porous media plug 1012 after compressed will have a central region 1013*h* with a greater porosity than an outer region 1016*h* away from the axis of the via 1006.

FIGS. 11A-11C depict a cross section of yet another illustrative embodiment of a fluidic device 1100 during pre and post insertion of porous media 1112 into a cavity of a fluidic device 1100. A porous media plug 1112 having a first shape, e.g., a flat disc, is positioned above an open end of a cavity 1110 formed in an exposed surface 1103 of a layer 1102 of the device 1100. The cavity 1110 extends along a sloped surface 1117 from a perimeter along the exposed surface 1103 to an orifice 1119 providing fluid communication between the cavity 1110 and the fluid channel or via 1106. A compressive force in a direction of the downward arrow urges at least a portion of the plug 1112 into the cavity 1110. In this example, a volume of the re-shaped or compressed plug 1112' is greater than a volume of the cavity 1110, such that a portion of the re-shaped plug 1112' remains above the surface 1103 when fully inserted into the cavity 1110. A portion of the re-shaped plug 1112' extending above the surface 1103 can be removed prior to use, resulting in a frit 1112" having a volume that corresponds to the volume of the cavity 1110.

Techniques for removal can include any of the machining techniques disclosed herein or otherwise known to those skilled in the art. In at least some embodiments, the exposed portion can be removed in whole or in part by an abrasive technique, such as polishing to provide a smooth transition between the frit 1112" and the surface 1103.

FIGS. 12A-12C depict a cross section of yet another illustrative embodiment of a fluidic device in which a porous media plug 1212 is press-fit into an open-ended cavity 1210 providing a curved surface 1217'. The curved surface 1217 extends from an outer perimeter of the cavity 1210 at a surface 1203 of the device to an orifice 1219 providing fluid communication between the cavity 1210 and a fluid channel 1206. The curved surface 1217 can conform to one or more of e.g., spherical, parabolic, catenary, polynomial shapes, and the like. Once again, an excess portion of the re-shaped plug 1212' can be removed leaving a flush, re-shaped frit 1212" having the target porosity profile.

Creating the low or zero porosity region 424, 724, 824, 924, 1016 *d*, 1016*f*, 1016*h*, 1309, 1409 is not limited to mechanical compression. The low or zero porosity region can also be achieved by melting, fusing or otherwise closing pores of a perimeter region. Melting of particular regions of the frit can be accomplished using one or more of a laser, an electron beam or other thermal means. Such melting or fusing techniques can be implemented prior to insertion of the frit into a device, during the insertion process and/or after the frit has been inserted into the device.

Figures 13A, 13B, 13C:
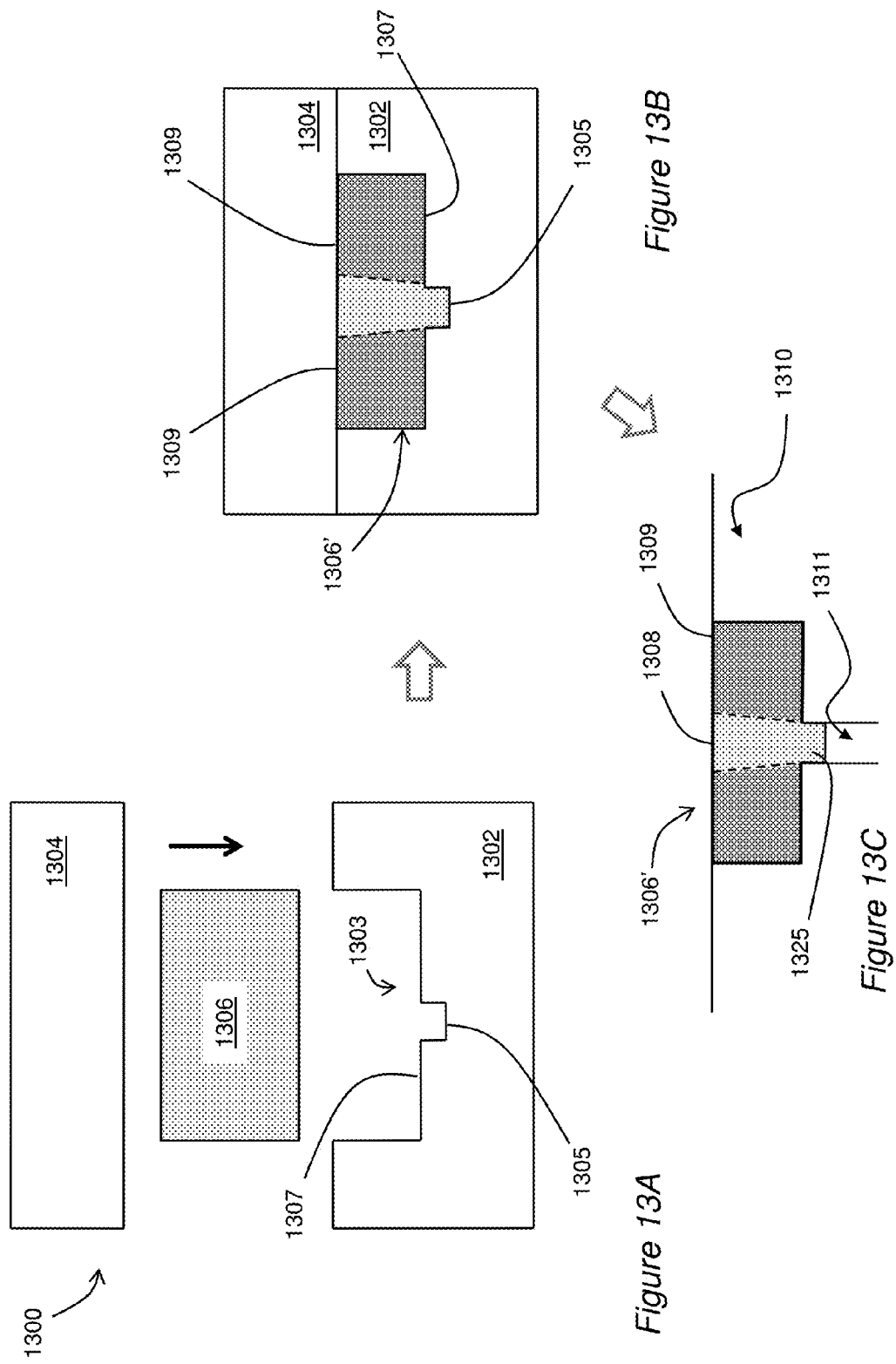
FIGS. 13A-13C depict cross sections of an illustrative embodiment of pre-formed frit during preforming to post insertion.

Referring next to FIGS. 13A and 13B, a porous member or frit 1306' can be prefabricated to have a target porosity prior to insertion into a fluid processing device 1310. At least one technique for prefabricating such a frit includes inserting a porous media member 1306 into tool 1300 having at least two parts according to a press-working technique. In the illustrative example, the press-working tool 1300 includes a die portion 1302 and a punch portion 1304. The porous media member or plug 1306, representing a work piece, is positioned between the die portion 1302 and the punch portion 1304. In operation, the press-working tool 1300 through a press-working action, exerts a force upon the work piece 1306. Namely, the die and the punch portions 1302, 1304 are urged together as indicated by the downward arrow, such that a portion of the porous media plug 1306 positioned between the two portions 1302, 1304 is entrapped therebetween. In the illustrative example, a thickness of the porous media plug 1306 is greater than a height between the die 1302 and punch 1304 during press-working. Accordingly, the press-working action exerts a compressive force on the entrapped portion of the plug of porous media 1306.

In some embodiments, the porous media plug 1306 has an initial or baseline porosity profile. By way of illustrative example, the baseline porosity profile can exhibit a uniform porosity that is substantially uniform across an expanse of the plug 1306. In the illustrative example, a mantle or stamping surface 1303 of the die portion 1302 contains a recessed surface area 1305. Namely, the recessed surface area 1305 includes a surface that is displaced at a height below a surrounding surface area 1307 of the stamping surface 1303. When the punch 1304 is pressed against the die 1302, the porous media plug 1306 is deformed or otherwise shaped into a compressed frit 1306', as shown in FIG. 13B. A central or inner portion 1308 of the frit 1306 experiences little or no compression, while a perimeter or outer portion 1309 is compressed so that the porosity becomes zero or very small. The result is a compressed frit 1306' having a protrusion 1325 along one surface. In some embodiments, when the compressed frit 1306' is inserted into a microfluidic device 1310, the protrusion 1325 can extend into an open end of a via 1311, and/or into a counterbore (not shown), when present between the open end of the via 1311 and the cavity 1310.

In the illustrative example, a predetermined portion of the compressed frit 1306', e.g., a central portion 1308, experiences little or no compression as a result of the displaced surface area 1305 being farther from the punch 1304 than the surrounding surface area 1307. Consequently, a portion of the frit 1306', e.g., an outer or perimeter portion 1309, is compressed such that the porosity of the perimeter region 1309 becomes substantially smaller than the porosity of the central region 1308.

When the compressed frit 1306' is inserted into the fluidic device 1310, as shown in FIG. 13C, the center portion 1308 can align with, and in some instances, insert into a proximal portion of a fluid channel, e.g., a via 1311 of the device 1310. The result is comparable to the porosity profiles disclosed in reference to FIGS. 4B, 7B and 8B, with a difference being that the compressed frit 1306' has been prefabricated, e.g., by press working, prior to insertion into the fluidic device 1310.

In another embodiment, shown in FIGS. 14A and 14B, a frit 1406' having a target porosity profile can be prefabricated prior to insertion into a fluid processing device. In particular, the frit 1406' can be re-shaped from a porous member 1406 having a non-uniform dimension, such as a non-uniform cross sectional shape and/or thickness. The first shape having the first porosity profile can be adjusted and/or re-shaped according to any of the techniques disclosed herein to produce a device having target porosity profile.

Once again, a press working technique can be used to re-shape the porous member, albeit, starting from a non-uniform shape/thickness. In the illustrative example, instead of providing a die 1402 with a recess, the plug of porous media 1406 is provided with a uniform baseline porosity and a non-uniform thickness or height. A plug of porous media 1406 is positioned between the die portion 1402 and the punch portion 1404. In operation, the press working tool 1400 exerts a press working action or force, e.g., a compressive force, upon the work piece 1406. Namely, the die and the punch portions 1402, 1404 are urged together as indicated by the downward arrow, such that a portion of the plug of porous media 1406 positioned between the two portions 1402, 1404 is entrapped therebetween. The press working action exerts a compressive force on the entrapped portion of the plug of porous media 1406.

In the illustrative example, a bottom surface 1413 of the plug of porous media 1406 contains a recess 1415, e.g., a cup. When the punch 1404 is pressed against the die 1402, which is flat, the plug of porous media 1406 is deformed or otherwise shaped into a pre-compressed frit 1406', as shown in FIG. 14B. Once again, a center portion 1408 of the frit 1406' experiences little or no compression, while an outer or perimeter region 1409 is compressed such that the porosity of the perimeter region 1409 becomes substantially smaller than the porosity of the central region 1408.

When the pre-compressed frit 1406' is inserted into a fluidic device 1410, as shown in FIG. 14C, the uncompressed region 1408 aligns with a via 1411. The result is comparable to the porosity profiles disclosed in reference to FIGS. 4B, 7B and 8B, with the difference being that the prefabricated, or shaped frit 1406' has been fabricated prior to insertion into the fluidic device 1410. The compressive forces transforming the plug of porous media 1406 to the frit 1406' having a target porosity profile are applied prior to insertion of the frit 1406' into the fluidic device 1410. Nevertheless, the frit 1406' can have a size that is substantially larger than a cross sectional diameter of the via 1411, while tending to confine fluid flow through the frit to a central region 1408 aligned with the via, thereby reducing dead volume attributable to unwanted fluid flow into the perimeter or outer regions 1409.

Figure 15A:
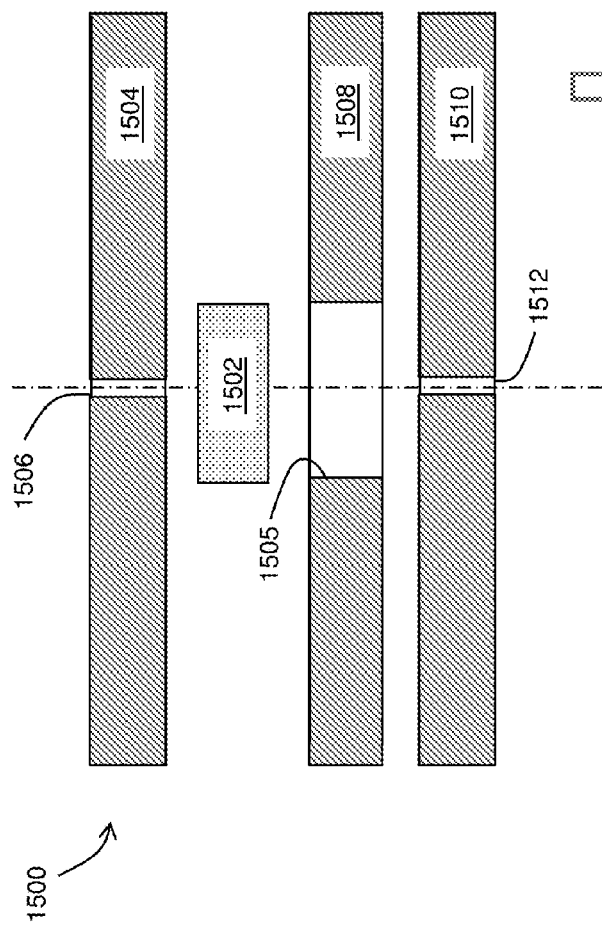
FIGS. 15A and 15B depict an illustrative embodiment of porous media in a three-layer fluidic device.
Figure 15B:
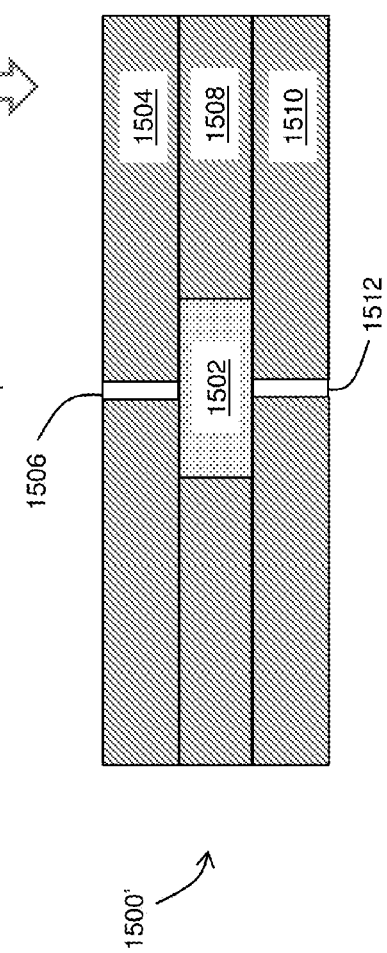

FIGS. 15A and 15B depict an illustrative embodiment of a planar microfluidic device 1500 in which a porous member, frit 1502', is integrated inside the device 1500 during fabrication. In at least some embodiments, the frit 1502 can be used to filter a fluid. For example, in a liquid chromatography system the frit 1502 filter can be positioned after a pump and before injection of a sample of a fluid.

The example planar microfluidic device 1500 consists of three layers, an upper layer 1504, an intermediate or middle layer 1508 and a lower layer 1510, fastened together by diffusion bonding. It is understood that such porous members can be used in other planar microfluidic devices having more or less than three layers. The upper layer includes an upper hole or via 1506 perpendicular to a planar surface of the upper layer 1504. The via 1506 allows for fluidic access to the frit 1502. The middle layer 1508 includes an aperture forming a through-cavity 1505 and the lower layer 1510 includes a lower via 1512. During fabrication, the porous member 1502 is positioned or otherwise placed inside the cavity 1505. Placement can include a frictional engagement and/or gaps between an outer perimeter of the frit 1502 and walls of the cavity 1505. The upper and lower layers 1504, 1510 are aligned with the middle layer 1508, such that the two vias 1506, 1512 are aligned with each other and the porous medium 1502 along a common axis. After assembly of the three layers and subsequent joining by diffusion bonding, a monolithic device 1500' is formed. The frit 1502 is encapsulated within the device 1500'. A fluid flowing into one of the vias 1506, 1512 is filtered by the porous frit 1502, such that a filtered fluid flows out an opposing one of the vias 1506, 1512.

In microfluidic applications, diameters of fluid channels tend to be exceedingly small to accommodate the minute fluid volumes processed by such devices. Mechanical insertion or application of a frit, e.g., insertion of a pre-formed porous member into a cavity or channel, in such applications would tend to be impractical if not impossible. According to the techniques disclosed herein, planar microfluidic devices are configured to accommodate porous members that are substantially larger than the diameters of the fluid channels with which they are used.

In the illustrative example, the frit 1502 is pre-formed as a planar disc having a thickness comparable to a thickness of the middle layer 1508 within which it is inserted, and a diameter that is consistent with a diameter of the cavity 1505 within which it is inserted. The direction of fluid flow is perpendicular to the plane of the frit 1502. In the illustrative example, the diameter of the frit 1502 is ten or more times the diameter of the channel diameter of the vias 1506, 1512. The relatively large size of the frit 1502 as well as the corresponding size of the cavity 1505 allow the frit 1502 to be handled with conventional tools allowing it to be manipulated and inserted into the cavity 1505. Beneficially, such mechanical insertion of the frit 1502 would be possible despite the exceedingly small diameters of the fluid channels 1508, 1510.

Although the use of porous media is disclosed in combination with planar microfluidic devices, it is understood that similar devices and techniques can be used in other fluid processing applications, without limitation. Namely, the use of pre-formed porous members can be applied to fluid processing channels having dimensions that are substantially smaller than dimensions of the porous medium. It should also be understood that although reference is made to incorporation of pre-formed porous members, some deformation, e.g., compression, can be applied to the pre-formed porous member during assembly. It should also be understood that the frit 1502 can include a uniform porosity profile, or a non-uniform, e.g., "tailored" porosity profile according to any of the techniques disclosed herein. Uniform porosity profiles can be used for applications in which peak broadening is not a concern. Examples of such applications include filters and/or pressure sensors of liquid chromatography systems.

Figure 16A:
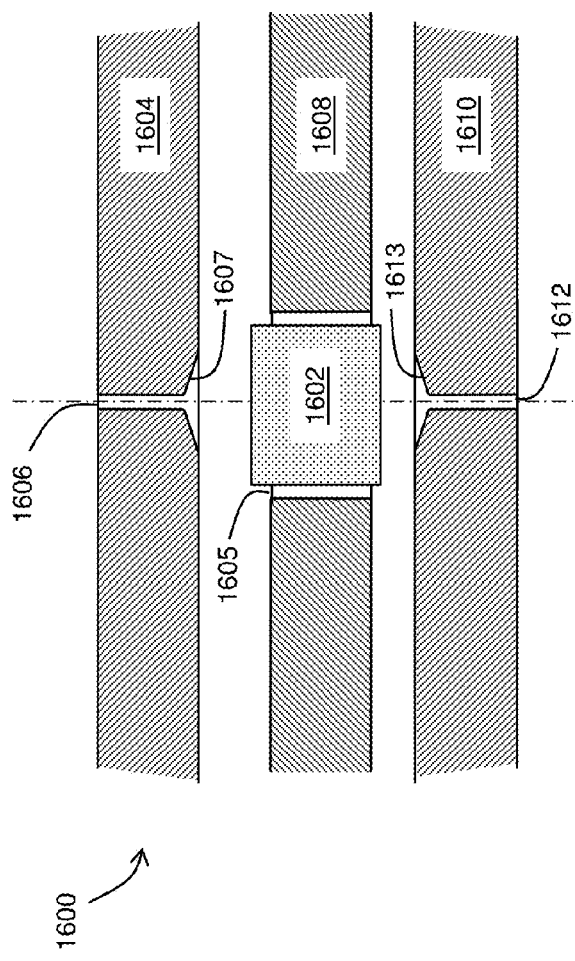
FIGS. 16A and 16B depict another illustrative embodiment of porous media in a three-layer fluidic device.
Figure 16B:
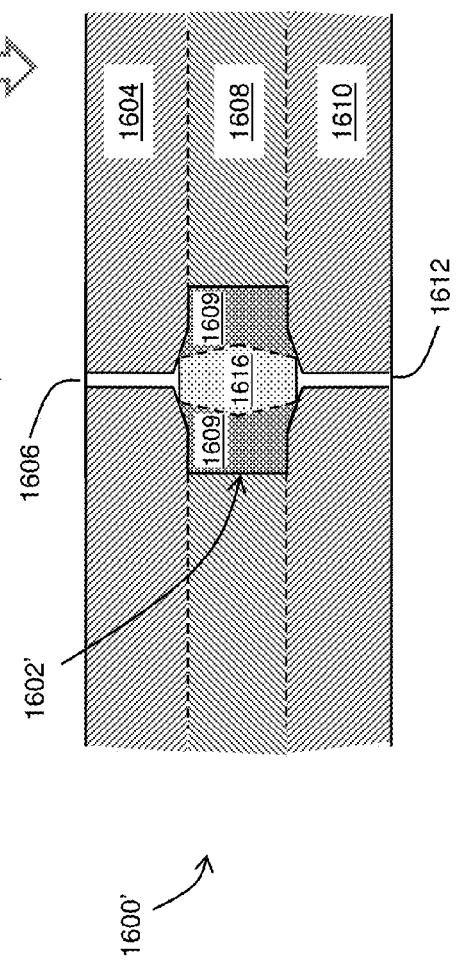

FIGS. 16A and 16B depict another illustrative embodiment of porous media in a three-layer fluidic device, in which a frit 1602' is integrated inside a fluidic device 1600 during fabrication of the device 1600. In at least some embodiments, the frit 1602' can be used to filter a fluid and/or in combination with a chromatographic column. The example fluidic device 1600 consists of three layers, an upper layer 1604 with a vertical hole or via 1606 for fluidic access, a middle layer 1608 with an aperture forming a through-cavity 1605, and a lower layer 1610 also including another via 1612. Devices with greater or fewer number of layers are possible. During fabrication, a porous member 1602 is placed inside the cavity 1605. The upper and lower layers 1604, 1610 are aligned with the middle layer 1608, such that the two vias 1606, 1612 are aligned with each other and the porous member 1602. After compression of the three layers and subsequent joining, for example using diffusion bonding, a monolithic device 1600' is formed.

In the illustrative example, a thickness of the porous member 1602 before joining is larger than a thickness of the middle layer 1608. When joined, the middle layer 1608 forms an intimate alignment abutting each of the upper and lower layers 1604, 1610. A joining force used to bring the layers together can also serve to compress at least a portion of the porous member 1602, thereby changing a shape of the porous member 1602 by compression. By its physical make up, the porous member 1602 can be compressed without breaking, fracturing or otherwise destroying a physical integrity of the porous member 1602. Consequently, a bulk volume of the porous medium is reduced, resulting in a corresponding reduction in porosity.

The porous member 1602 can be compressed uniformly between the upper and lower layers 1604, 1610. Alternatively, one or more portions of the porous medium 1602 can be compressed to differing degrees with respect to other portions. In the illustrative example, the upper layer 1604 includes a shaped cavity, e.g., a conical cavity 1607, centered around an orifice to the upper via 1606. Likewise, the lower layer 1610 includes a complementary conical cavity 1613, centered around an orifice to the lower via 1612. Upon joining, a frit 1602' is formed in the cavity 1605 joining the two vias 1606, 1612. The formed frit 1602' includes a central portion 1616 of the porous member 1602 nearer to an axis of the vias 1606, 1612 that is compressed less than outer portions 1609 of the porous medium 1602 farther away from the axis. Consequently, the central portion 1616 of the formed frit 1602' retains a porosity that is relatively higher than a porosity of the outer regions 1609. In operation, such a modified porosity profile can preferentially allow fluid to flow through the central portion 1616, while inhibiting flow into the outer portions 1609.

It is understood that the cavities 1607, 1613 can take on any of the shapes disclosed herein, including combinations of such shapes and equivalents. It should also be understood that the one or both of the cavities 1607, 1613 can be absent, e.g., adjacent layers presenting a flat surface to each other. It is further understood that a shape of the upper cavity 1607 can be equivalent to or different from a shape of the lower cavity 1613. In some embodiments, one or both of the upper and lower layers 1604, 1610 do not contain a cavity 1607, 1613. In some embodiments, the porous member 1602 has a uniform thickness before joining. Alternatively, the porous member 1602 can have a non-uniform thickness before joining. For example, the thickness can be sloped or otherwise shaped according to various profiles, including linear shaped profiles, curvilinear shaped profiles, discontinuous shaped profiles and/or combinations of such various profiles. Alternatively or in addition, the porosity of the porous member 1602 before joining can be uniform, or otherwise constant across the porous member 1602. Alternatively, the porosity before joining can be non-uniform, e.g., having a lower porosity in a central region that is aligned with the vias when joined. A target porosity profile can be achieved according to any of the techniques disclosed herein. In some applications, the porous member 1602 experiences substantially no compression, such that the target porosity profile is equivalent to the initial porosity profile.

Figure 17:
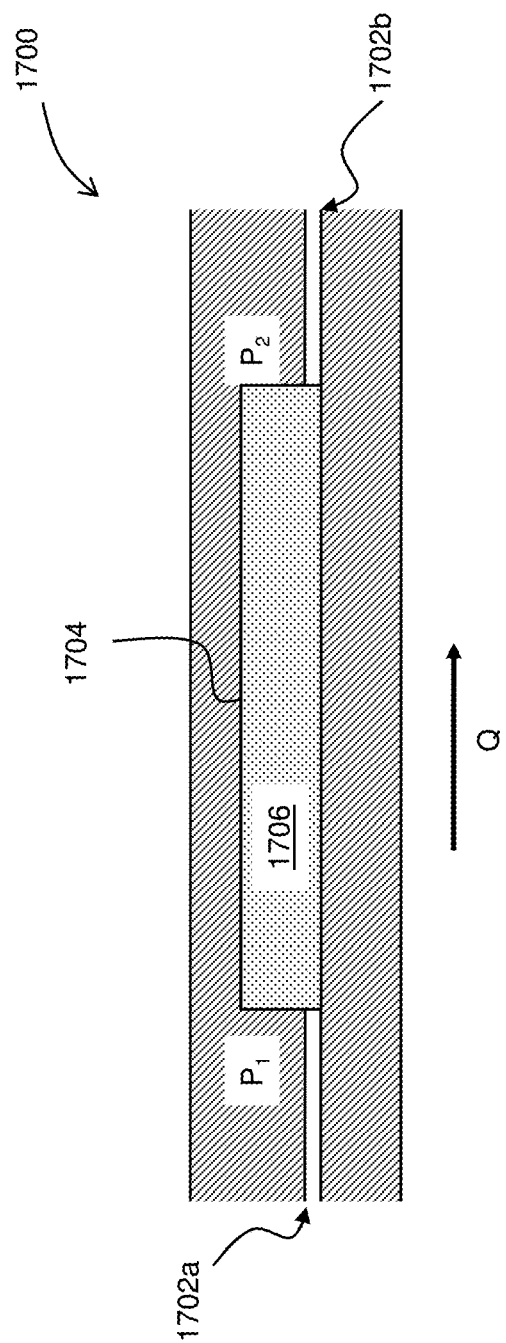
FIG. 17 depicts a cross section of a porous media used as a flow restrictor.

FIG. 17 depicts an illustrative embodiment of a cross section of a porous media 1706 used as a flow restrictor. The device 1700 includes a first fluid channel 1702a having one end abutting a first end of a cavity 1704 formed in the device 1700. The cavity 1704 contains a porous media member or plug 1706. The device 1700 also includes a second fluid channel 1702b having one end abutting a second end of the cavity 1704. In the illustrative embodiment, the first and second fluid channels are in axial alignment on opposite sides of the porous member 1706.

The porosity of the porous member 1706 presents a flow restrictor to a fluid flowing through the device, along the fluid channels 1702a, 1702b. As a consequence of the flowing fluid in the presence of the fluid restriction of the porous member 1706, a pressure differential is developed across the porous member 1706. A first pressure $P_1$ is present along a first end, e.g., within the first fluid channel 1702a, whereas a different pressure $P_2$ is present along a second end, e.g., within the second fluid channel 1702b. With a fluid flow Q in the direction indicated, the pressure $P_1 > P_2$. The porosity of the porous member can be adjusted or otherwise tailored according to any of the techniques disclosed herein. By adjusting a porosity profile to a target porosity profile, a preferred pressure differential can be obtained. In at least some embodiments, the device 1700 can include one or more pressure sensors (not shown), e.g., positioned at one or more of the fluid channels 1702a, 1702b. Such flow rate sensors can be used to determine a pressure difference, e.g., across a fluidic resistance of the porous member 1706.

Figure 18:
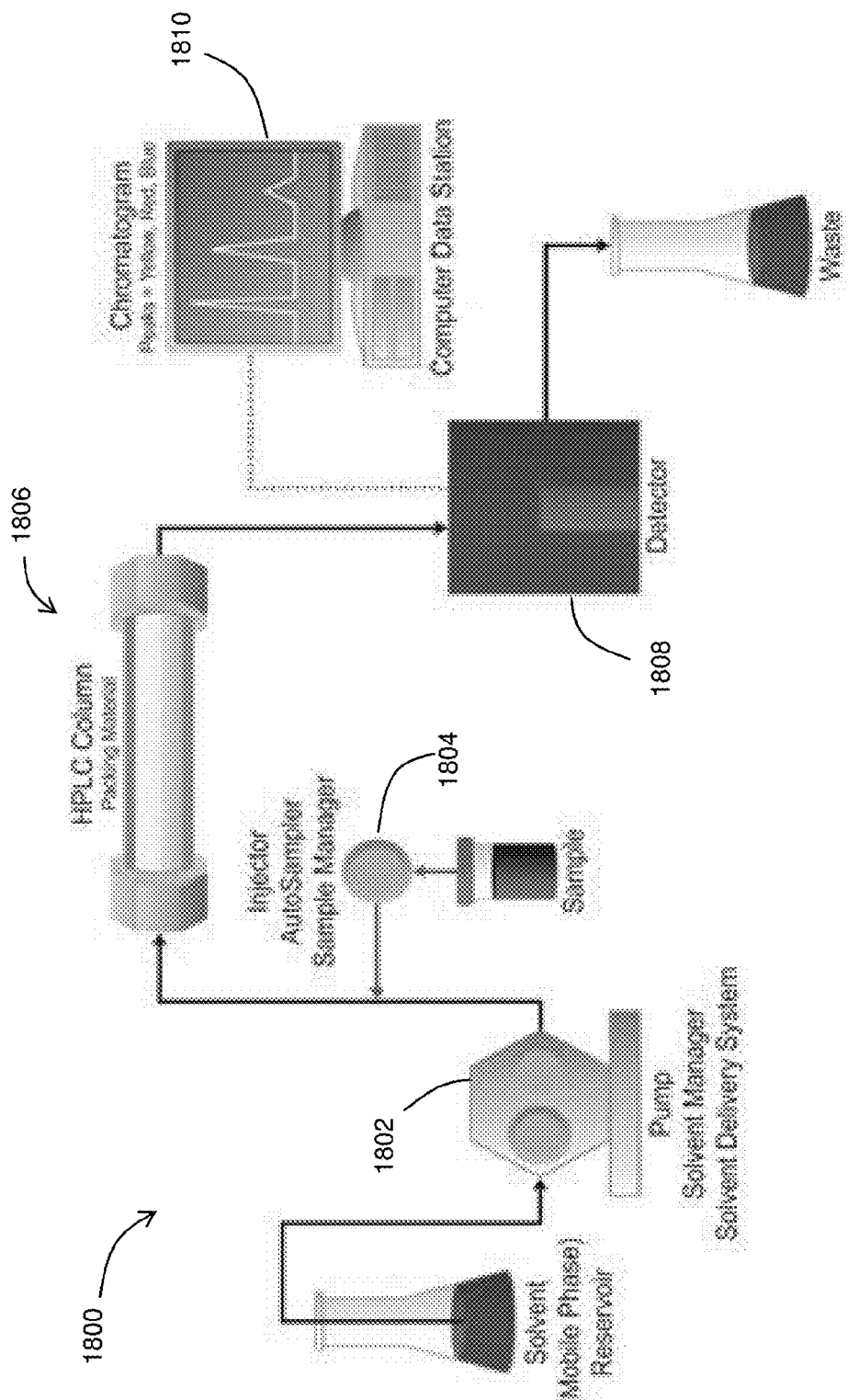
FIG. 18 depicts an illustrative embodiment of a liquid chromatography fluid processing system.

FIG. 18 depicts an illustrative embodiment of a liquid chromatography fluid processing system 1800 that can utilize singly or in combination any of the embodiments of the subject disclosure. The system 1800 includes at least the following components: a pump 1802, an injector 1804, a chromatographic column 1806, a detector 1808, and a computer 1810 running software capable of data acquisition and processing. The pump 1802 can be used to propel a liquid stream through the injector, column 1806, and detector 1808. The injector 1804 can be operably connected to the pump 1802 to permit the introduction of a liquid sample into the liquid stream prior to its entering the column 1806. Sample components can then separate as they migrate through the column 1806 by means of a variety of interactions between the solutes and the packing material contained therein. The column can use any of the embodiments of the subject disclosure for controlling the porosity profile of a frit at either or both ends of the column 1806. Upon exiting the column 1806, the individual components can be detected by the detector 1808, before being discarded. A signal from the detector 1808 can then be processed by a suitable computer software program executed by the computer 1810 to provide a numerical value and/or graphical depiction indicating the amount of solute detected.

Figure 19:
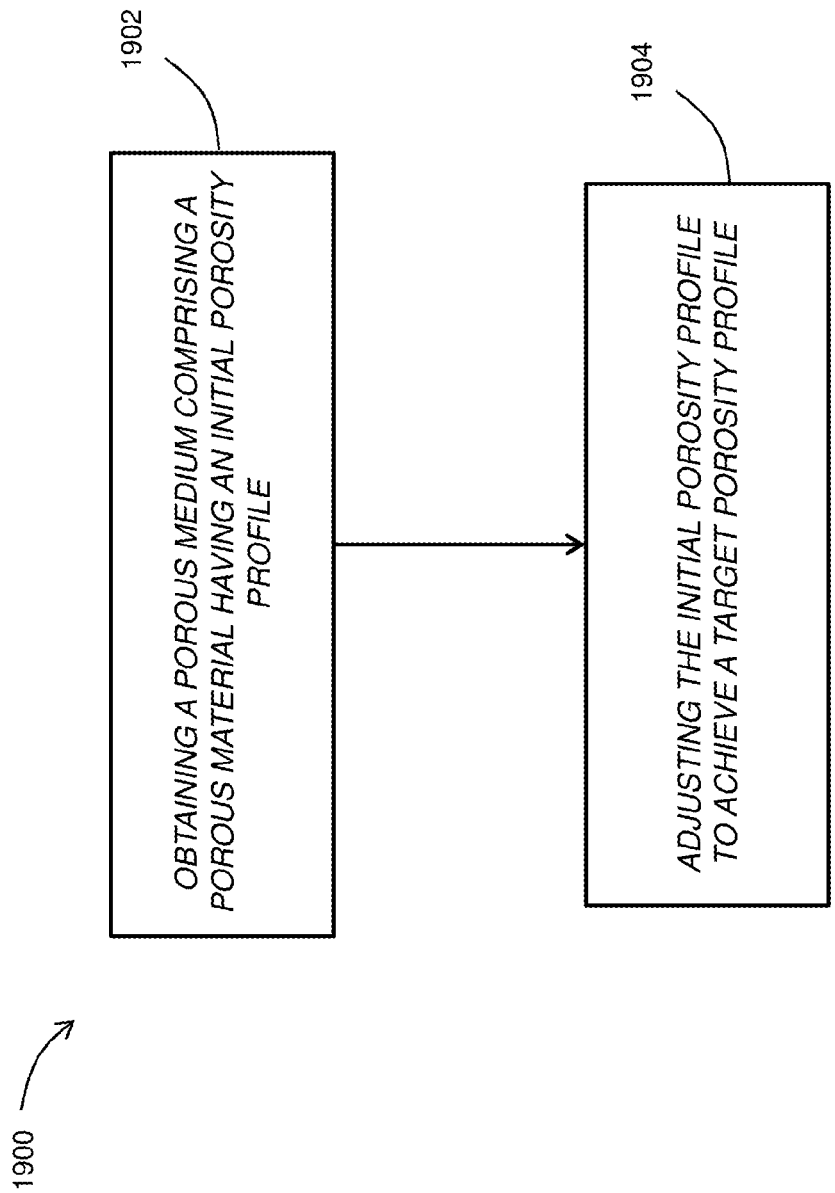
FIG. 19 depicts an illustrative embodiment of a process for transforming a porosity profile of a porous material.

FIG. 19 depicts an illustrative embodiment of a process 1900 for transforming a porosity profile of a porous material. Method 1900 begins obtaining at step 1902 a porous medium that includes a porous material having a first shape and an initial porosity profile. In one embodiment, the porous medium can be engaged with a cavity to achieve a target porosity profile. The engaging of the porous material and the cavity causes a first shape of the porous material to be adjusted to a second shape. Readjustment of the shape of the porous material can result in the initial porosity profile being adjusted to the target porosity profile. The shape of the porous material can be altered by the shape of the cavity, the shape of a mantle compressing the porous material into the cavity, the first shape of the porous material or a combination thereof. The readjusting of the shape of the porous material is done intentionally to achieve the target porosity profile. The process of method 1900 can also be used to prefabricate porous materials with a target porosity profile which is then engaged with a preformed cavity that maintains the target porosity profile.

Upon reviewing the aforementioned embodiments, it would be evident to an artisan with ordinary skill in the art that said embodiments can be modified, reduced, or enhanced without departing from the scope of the claims described below. For example, it is understood that the shape of a cavity can take on any conceivable shape. For example, the cavity viewed in an axial cross section can include alone or in combination one or more of flat walls (i.e., parallel to a surface of the device), sloped walls, stepped walls, curved walls, and so on. The cavity can introduce a convex contour to a frit formed thereon. Alternatively or in addition, the cavity can introduce a concave contour upon the frit. Although the illustrative examples disclosed herein discuss advantages of providing frits having a greater porosity along a central region, e.g., aligned with an axis of an abutting fluid channel, it is by no means limiting. It is conceivable that in at least some applications, the central region of the frit can be configured to offer a lower porosity (i.e., being compressed or shape-altered more than outer regions of the frit). Such frits can be useful in promoting a mixing of fluids and/or introducing a delay into a fluid flow.

Likewise, it is understood that the shape of punch face or mantle can take on any conceivable shape, including any of the shapes disclosed herein in reference to the cavity. Open end cavities in some embodiments include sidewalls, as disclosed herein, while others do not. Namely a non-planar cavity can extend upward, terminating along a surface of the device, instead of terminating along a separate side wall. Side walls can also take on various configurations. For example, the side walls can be perpendicular to the surface of the device, angled to the surface, straight, curved, stepped, and so forth. One or more of the floor and sidewalls can include one or more ridges or grooves or similar features to promote or otherwise facilitate an interference fit of the frits within the cavity. In at least some embodiments, such grooves can impart a sufficient change in shape to introduce a measurable change in porosity.

Frits can be made from various materials, such as porous media, e.g., porous metal media. Porous metal media is a unique material that exhibits a wide range of definable flow and filtration properties. Porous material can be fabricated from packing and sintering a particulate material, such as stainless steel or titanium. Other particulate material suitable for porous media include, without limitation, nickel, Inconel®, Hastelloy®, titanium, and others. Inconel® is a registered trademark of Inco Alloys International, Inc., of Huntington, W. Va. Hastelloy® is a registered trademark of Haynes International, Inc., of Kokomo, Ind. Such materials can be chosen, e.g., according to an end-use application to provide necessary physical properties, such as strength, heat resistance, corrosion resistance, and process compatibility. Prepared porous material can be obtained from a supplier, e.g., Mott Corp of Farmington, Conn.

The porous devices disclosed herein can be fashioned or otherwise cut or separated from these larger sheets. For example, a preferred shape, such as a disc, a square, a diamond or oval can be cut out from the larger sheet of porous material. Cutting can be accomplished by any suitable means, including die cutting, rotary die cutting, machining, micromachining, electrical discharge machining (EDM), e.g., wire-cut, electron beam machining (EBM), laser cutting, water jet cutting, electrochemical erosion.

Figure 2:
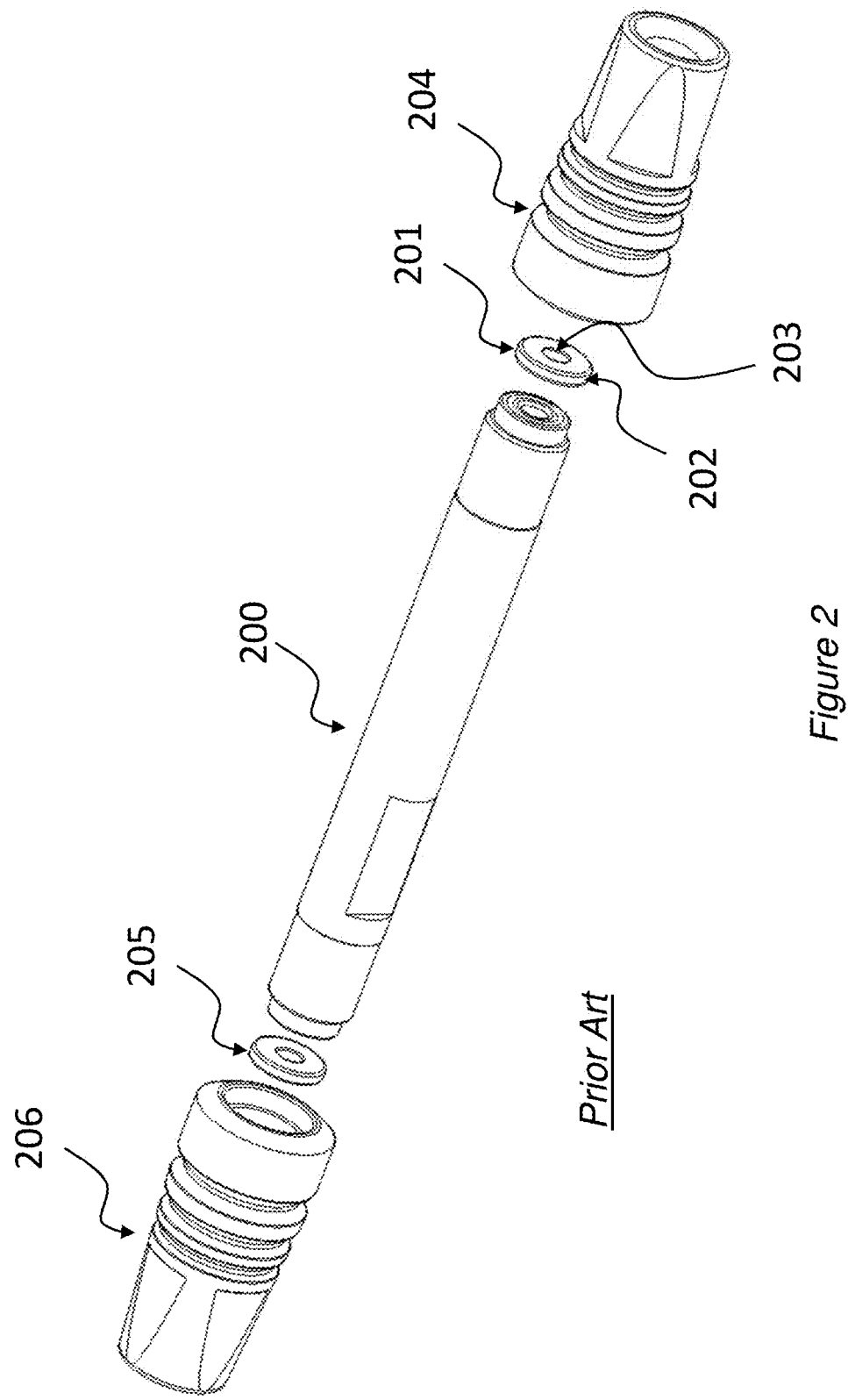
FIG. 2 depicts an exploded view of a prior art liquid chromatography column.

Many of the frits and cavities disclosed herein have been illustrated in axial profile. It is understood that such example profiles are provided without limitation as to a planar configuration of the aperture and/or the open-end cavity. For example, the cavity can be rotationally symmetric about a central axis, e.g., the axis of an abutting fluid channel or via. Thus, the planar configuration of the cavity, and/or porous media plug, and/or frit can be circular, elliptical, square, rectangular, polygonal, presenting a symmetric profile or an asymmetric profile. It is also understood that any of the embodiments disclosed herein can be used in non-planar configurations, such as the tubular configuration illustrated in FIG. 2. It is also understood that variations in porosity need not be confined to an inner or central region of a frit. Namely, a frit can have a flow region of greater porosity that is not centrally located, e.g., off center and/or along one or more edges compared to other regions of the frit having relative low or zero porosity. It is also understood that a single frit can be fabricated with more than one distinguishable regions having a non-zero porosity to promote a confined flow within a compressed or otherwise modified frit having regions with a relatively low, e.g., approaching zero, porosity.

The geometry of the devices disclosed herein are scalable. For applications involving extremely small quantities of fluid, e.g., microliters, nanoliters, picoliters, femtoliters, the device can be scaled appropriately. Although the examples disclosed herein refer to planar fluidic devices, it is understood that other non-planar configurations are possible.

Various insertion and/or compressive forces are disclosed herein as acting upon a porous media plug to transform the plug into a frit having a porosity profile that approaches a target porosity profile. The forces can be applied to the plug before, during and/or after insertion of the plug into the cavity of the device. Although the forces have largely been disclosed as resulting from press-fitting or axial compression of the plug, it is understood that other transformative forces are possible. For example, radial forces can be provided externally, e.g., by a radial compression die and/or by a radial configuration of one or more of the punch and the cavity or die. In some instances, the forces can include a torsional component. For example, a punch may impart a torsional force or torque upon at least a portion of the porous media plug. For applications in which the plug is retained, e.g., by a feature of the cavity, such as a wall and/or a ridge, the torsional force can impart a change in shape that alters the porosity of the plug.

It should be understood that devices described in the exemplary embodiments can be used alone or in combination with other fluid processing devices according to fluid processing methodologies, including the chemical separation and analysis devices and processes disclosed in International Application No. PCT/US2010/026342, entitled "Electrospray Interface to a Microfluidic Substrate," incorporated herein by reference in its entirety. The methodologies can be fluid links that are described as coupled, connected and so forth, which can include unidirectional and/or bidirectional fluid communication over fluid channels according to fluid transfer methodologies, where the coupling and/or connection can be direct (e.g., no intervening fluid processing device) and/or indirect (e.g., an intermediary fluid processing device, such as a pump, a mixer, or a detector).

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, can be used in the subject disclosure.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:
1. A method, comprising:
    obtaining a porous medium comprising a porous material having a first shape and an initial porosity profile; and
    engaging the porous medium with a cavity in a fluidic device, wherein the cavity is in fluid communication with a channel of the fluidic device, wherein the engaging of the porous medium with the cavity causes the first shape of the porous material to be adjusted to a second shape resulting in the initial porosity profile being adjusted to a target porosity profile, wherein the target porosity profile comprises an inner region having a first porosity and an outer region having a second porosity that differs from the first porosity, wherein the inner region and the outer region are aligned along a common axial reference location.
2. The method of claim 1, wherein the fluidic device comprises a microfluidic device, and wherein the target porosity profile directs a fluid flow through the porous medium in proximity to an opening of the channel to reduce fluid diffusion.

3. The method of claim 1, wherein a third shape of the cavity during the engaging of the porous medium with the cavity, results in the target porosity profile.

4. The method of claim 3, wherein the engaging comprises compressing the porous material against a floor of the cavity, wherein the floor is non-planar.

5. The method of claim 1, wherein a fourth shape of a mantle utilized in the engaging of the porous medium with the cavity, results in the target porosity profile.

6. The method of claim 1, wherein the engaging of the porous medium with the cavity comprises compressing of the porous material causing a non-uniform porosity profile varying laterally across the porous medium.

7. The method of claim 1, wherein the engaging of the porous medium with the cavity causes the porous medium to be retained with respect to the cavity when subjected to a fluid flow through the channel.

8. The method of claim 1, wherein the initial porosity profile is uniform and the target porosity profile is non-uniform.

9. The method of claim 1, wherein the inner region of the target porosity profile includes a higher porosity than the outer region of the target porosity profile, wherein the inner region is in proximity to an opening of the channel, and wherein the outer region is remote from the opening of the channel, wherein the inner region extends from a fluid inlet surface of the porous medium to a fluid exit surface of the porous medium.

10. The method of claim 1, wherein an opening of the channel is an inlet of the channel, wherein the porous material comprises sintered particles.

11. The method of claim 1, further comprising providing a bed of particles in the fluidic device, wherein the target porosity profile of the porous material prevents flow of the bed of particles through the porous medium.

12. The method of claim 11, further comprising:
obtaining a second porous medium; and
engaging the second porous medium with a second cavity in the fluidic device, wherein the second cavity is in fluid communication with the channel of the fluidic device, wherein the second porous medium has a porosity profile that allows flow of a fluid through the second porous medium and prevents flow of the bed of particles through the second porous medium.

13. The method of claim 1, wherein the target porosity profile comprises a sloped porosity profile in which a change in porosity between the inner region and the outer region varies according to a slope that directs a fluid flow through the porous medium in proximity to an opening of the channel to reduce fluid diffusion.

14. The method of claim 1, wherein the target porosity profile comprises a curved porosity profile in which a change in porosity between the inner region and the outer region varies according to a curve that directs a fluid flow through the porous medium in proximity to t opening of the channel to reduce fluid diffusion.

15. The method of claim 1, wherein the initial porosity profile comprises a substantially uniform porosity.

16. A method, comprising:
obtaining a porous medium comprising a porous material having a non-uniform porosity profile that provides different porosities at different radial displacements from a common reference location along a fluid axis; and
engaging the porous medium with a cavity in a fluidic device, wherein the cavity is in fluid communication with a channel of the fluidic device, wherein the non-uniform porosity profile is selected for directing a fluid flow along the fluid axis through the porous medium in proximity to an opening of the channel to reduce fluid diffusion,
wherein the non-uniformity porosity profile comprises a first region of the porous material at a first radial displacement from the common reference location along the fluid axis having a higher porosity than a second region of the porous material at a second radial displacement from the common reference location along the fluid axis, wherein the first region is in proximity to the opening of the channel, wherein the second region is remote from the opening of the channel, and wherein the first region extends from a top surface of the porous medium to a bottom surface of the porous medium.

17. The method of claim 16, wherein the different porosities at the different radial displacements vary according to a sloped porosity profile that directs a fluid flow through the porous medium in proximity to opening of the channel to reduce fluid diffusion away from the opening of the channel.

18. The method of claim 16, wherein the different porosities at the different radial displacements vary according to a curved porosity profile that directs a fluid flow through the porous medium in proximity to opening of the channel to reduce fluid diffusion away from the opening of the channel.

19. The method of claim 16, wherein the different porosities at the different radial displacements vary according to a stepped porosity profile that directs a fluid flow through the porous medium in proximity to opening of the channel to reduce fluid diffusion away from the opening of the channel.

* * * * *